United States Patent [19]

Ackermann et al.

[11] Patent Number: 5,532,232

[45] Date of Patent: *Jul. 2, 1996

[54] GUANIDINE DERIVATIVES

[75] Inventors: Jean Ackermann; David Banner, both of Basel, Switzerland; Klaus Gubernator, Freiburg, Germany; Paul Hadvary, Biel-Benken, Switzerland; Kurt Hilpert, Hofstetten; Klaus Müller, Münchenstein, Switzerland; Ludvik Labler, Bottmingen, Switzerland; Gérard Schmid, Kienberg, Switzerland; Thomas B. Tschopp, Ettingen, Switzerland; Hans P. Wessel, Heitersheim, Germany; Beat Wirz, Reinach, Switzerland

[73] Assignee: Hoffmann-La Roche Inc., Nutley, N.J.

[*] Notice: The term of this patent shall not extend beyond the expiration date of Pat. No. 5,405,854.

[21] Appl. No.: 343,168

[22] Filed: Nov. 22, 1994

Related U.S. Application Data

[62] Division of Ser. No. 77,476, Jun. 15, 1993, Pat. No. 5,393,760, which is a division of Ser. No. 719,429, Jun. 24, 1991, Pat. No. 5,260,307.

[30] Foreign Application Priority Data

Jul. 5, 1990 [CH] Switzerland ............... 2250/90
May 2, 1991 [CH] Switzerland ............... 1315/91

[51] Int. Cl.$^6$ .................. A61K 31/445; C07D 211/22; C07D 211/26
[52] U.S. Cl. .................. 514/183; 514/211; 514/212; 514/221; 514/237.2; 514/314; 540/315; 540/316; 540/320; 540/326; 540/331; 540/481; 540/544; 540/569; 544/130; 546/172; 546/189; 546/202; 546/212; 546/231; 546/233; 546/235; 546/246

[58] Field of Search .................. 546/189, 202, 546/212, 231, 233, 235, 246, 172; 540/315, 316, 320, 326, 331, 569, 544, 481; 544/130; 514/183, 211, 212, 221, 237.2, 314

[56] References Cited

U.S. PATENT DOCUMENTS

| 4,433,152 | 2/1984 | Muramatsu | 546/193 |
| 5,254,569 | 10/1993 | Cheeseman | 514/331 |
| 5,405,854 | 4/1995 | Ackermann | 514/315 |

*Primary Examiner*—Philip I. Datlow
*Attorney, Agent, or Firm*—George M. Gould; William H. Epstein; Bruce A. Pokras

[57] ABSTRACT

Compounds of the formula

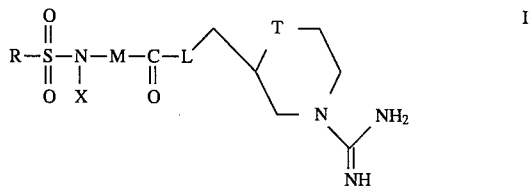

wherein L, M, R, T and X are set forth in the description, as well as hydrates or solvates thereof, which inhibit thrombin-induced platelet aggregation and clotting of fibrinogen in plasma, are described. The compounds of formula I are prepared by amidination or, depending on whether L is NH or O, by amide formation or esterification.

45 Claims, No Drawings

GUANIDINE DERIVATIVES

This is a division of application Ser. No. 08/077,476 filed Jun. 15, 1993 now U.S. Pat. No. 5,393,760, which is a divisional of Ser. No. 07/719,429 filed Jun. 24, 1991, now U.S. Pat. No. 5,260,307.

BRIEF SUMMARY OF THE INVENTION

The invention relates to guanidines derivatives of the formula

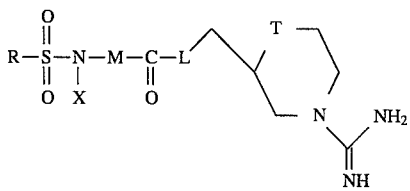

wherein

R is aryl, heteroraryl or heterocyclyl;

T is $CH_2$ or O;

L is NH or O; and —N(X)—M— is a —N($SO_2$—$R^o$)—$CH_2$— group, an isoquinolylene group optionally substituted in the phenyl ring and wherein $R^o$ has the same significance as R, or, individually, X is H, —$CH_2COOH$, —$CH_2COO$—$C_{1-4}$-alkyl, —$CH_2CO$— (tetra- to heptamethyleneimino) or optionally N-mono- or N-di-$C_{1-4}$-alkylated —$CH_2CONH_2$, M is a R'—$(CH_2)_{1-2}CH$=, R'—$COCH_2CH$=, R"—$COCH_2CH$=, R'—$(CO)_{1-2}NHCH_2CH$=, benzyl-$OCONHCH_2CH$=, —$CH_2$[R'—$(CO)_{1-2}NH$]CH—, —$CH_2$(benzyl-OCONH)CH— or —CH(CO—Q)$CH_2$— group, R' is aryl, heteroaryl, cycloalkyl or heterocyclyl, R" is tetra- to heptamethyleneimino optionally carrying up to 2 substituents from the group oxo, —COO—$C_{1-4}$-alkyl, —$(CH_2)_{0-1}OH$, —$(CH_2)_{0-1}OCO$—$C_{1-4}$-alkyl and optionally mono- or di-$C_{1-4}$-alkylated carbamoyl, and Q is benzylamino or a tetra- to heptamethyleneimino group optionally interrupted by an O or S-atom and optionally substituted by up to 2 substituents from the group $C_{1-4}$-alkyl, COOH, —COO—$C_{1-4}$-alkyl, —$CH_2OH$ and —$CH_2O$-benzyl, as well as hydrates or solvates and physiologically usable salts thereof.

DETAILED DESCRIPTION OF THE INVENTION

The invention relates to guanidine derivatives of the formula

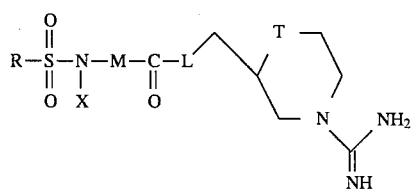

wherein

R is aryl, heteroraryl or heterocyclyl;

T is $CH_2$ or O;

L is NH or O; and —N(X)—M— is a —N($SO_2$—$R^o$)—$CH_2$— group, an isoquinolylene group optionally substituted in the phenyl ring and wherein $R^o$ has the same significance as R, or, individually, X is H, —$CH_2COOH$, —$CH_2COO$—$C_{1-4}$-alkyl, —$CH_2CO$— k (tetra- to heptamethyleneimino) or optionally N-mono- or N-di-$C_{1-4}$-alkylated —$CH_2CONH_2$, M is a R'—$(CH_2)_{1-2}CH$=, R'—$COCH_2CH$=, R"—$COCH_2CH$=, R'—$(CO)_{1-2}NHCH_2CH$=, benzyl-$OCONHCH_2CH$=, —$CH_2$[R'—$(CO)_{1-2}NH$]CH—, —$CH_2$(benzyl-OCONH)CH— or —CH(CO—Q)$CH_2$— group, R' is aryl, heteroaryl, cycloalkyl or heterocyclyl, R" is tetra- to heptamethyleneimino optionally carrying up to 2 substituents from the group oxo, —COO—$C_{1-4}$-alkyl, —$(CH_2)_{0-1}OH$, —$(CH_2)_{0-1}OCO$—$C_{1-4}$-alkyl an optionally mono- or di-$C_{1-4}$-alkylated carbamoyl, and Q is benzylamino or a tetra- to heptamethyleneimino group optionally interrupted by an O or S-atom and optionally substituted by up to 2 substituents from the group $C_{1-4}$-alkyl, COOH, —COO—$C_{1-4}$-alkyl, —$CH_2OH$ and —$CH_2O$-benzyl, as well as hydrates or solvates and physiologically usable salts thereof.

In other aspects, the invention is concerned with a process for the manufacture of the above compounds, pharmaceutical preparations which contain such compounds as well as the use of these compounds in the manufacture of pharmaceutical preparations.

Examples of physiologically acceptable salts of the guanidines of formula I are salts with physiologically acceptable mineral acids such as hydrochloric acid, sulfuric acid, sulfurous acid or phosphoric acid; or with organic acids such as methanesulfonic acid, p-toluenesulfonic acid, acetic acid, trifluoroacetic acid, citric acid, fumaric acid, maleic acid, tartaric acid, succinic acid or salicylic acid. The guanidines of formula I having a free carboxy group can also form salts with physiologically acceptable bases. Examples of such salts are alkali metal, alkaline earth metal, ammonium and alkylammonium salts such as the sodium, potassium, calcium or tetramethylammonium salt. The guanidines of formula I can also be present in the form of zwitterions.

The guanidines of formula I can be solvated, especially hydrated. The hydration can be effected in the course of the manufacturing process or can occur gradually as a result of hygroscopic properties or an initially anhydrous compound of formula I.

The guanidines of formula I contain at least two asymmetric C atoms and can therefore be present as mixtures of diastereomers or as the optically pure compound.

In the scope of the present invention, $C_{1-4}$-alkyl denotes straight-chain ($C_{1-4}$-n-alkyl) or branched groups such as methyl, ethyl, propyl, isopropyl, butyl, isobutyl and t-butyl.

Aryl denotes groups such as phenyl, naphthyl and anthryl, optionally with 1 to 4 substituents such as halogen, $NO_2$, $NH_2$, CN, OH, $CH_3$, isopropyl, t-butyl, phenyl, phenylsulfonyl, $OCH_3$, benzyloxy, formamido, COOH, COO—$C_{1-4}$-n-alkyl or optionally mono- or di-$C_{1-4}$-alkylated amino.

Examplary of other substituents on a phenyl group are —$NHSO_2$—Ar or —NHCO—Ar (wherein Ar is phenyl with up to 3 substituents such as halogen, $NO_2$, $CF_3$, COOH and $C_{1-4}$-alkyl, (for example, $CH_3$), —$NHCOCH_2CH_2COO$(H, $C_{1-4}$-alkyl or benzyl), acetamido, —NHCOCH$_2$OCH$_2$CH$_2$OCH$_3$, —NHCOO(H or $C_{1-4}$-alkyl), —NHCOCOO (H or $C_{1-4}$-alkyl), —NHCH$_2$COethyl, —NHCOCOC$_6$H$_5$ and tetra- to hepta-methyleneiminocarbonyl.

Cyclohexyl and decalyl are examples of cycloalkyl groups. Heteroaryl groups consist of one or 2 rings and contain 3 to 9 C atoms and 1 or 2 hetero atoms. Examples thereof are imidazolyl, thienyl, benzothienyl, quinolyl and indolyl. They can be substituted, for example, by CH$_3$, halogen, —CH$_2$COOH or 1-methyl-5-trifluoromethylpyrazolyl.

Heterocyclyl denotes groups containing 1 or 2 rings, 4 to 7 C atoms and 1 or 2 hetero atoms, such as tetrahydroquinolyl, azepinyl, piperidinyl, pyrrolidinyl, benzodiazepinyl, benzoxazolyl and benzopyrrolidinyl, optionally bearing 1 or 2 substituents such as methyl, halogen, oxo, COOH or COOCH$_3$.

Piperidino, hexahydroazepino and heptahydroazocino are examples of tetra- to heptamethyleneimino groups. Acetoxy, acetoxymethyl, carbomethoxy, caromethoxy, carbethoxy, diethylcarbamoyl, butyryloxymethyl and isobutyryloxymethyl are examples of substituents on group R".

Carboxyhexahydrooxazepino and hexahydrothiazepino are examples of tetra- to heptamethyleneimino groups which are interrupted by an O or S atom and which are optionally substituted.

Cl, NO$_2$, NH$_2$ and OH come into consideration, for example, as a substituent on the phenyl ring of an isoquinolylene group —N(X)—M.

Examples of compounds of formula I are those of the formula

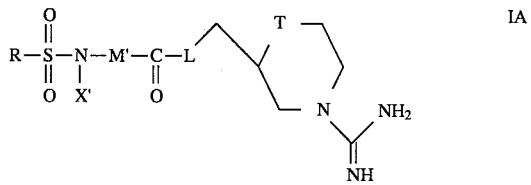

IA wherein

—N(X')—M'— is an isoquinolylene group optionally substituted on the phenyl ring, or, individually, X' is H, —CH$_2$COOH, —CH$_2$COO—C$_{1-4}$-alkyl, —CH$_2$CO— tetra- to heptamethyleneimino or optionally N- mono- or N-di-C$_{1-4}$-alkylated —CH$_2$CONH$_2$, M' is a R'—(CH$_2$)$_{1-2}$CH=, R'—COCH$_2$CH= or —CH(CO—Q')CH$_2$— group, and Q' is benzylamino, morpholino or tetra- to heptamethyleneimino and R,R',L and T are as previously described, as well as hydrates or solvates and physiological usable salts thereof.

Preferred among the compounds of formula IA are those in which X' is H and R,M',L and T are as previously described.

Preferred among the compounds I are those of the formula

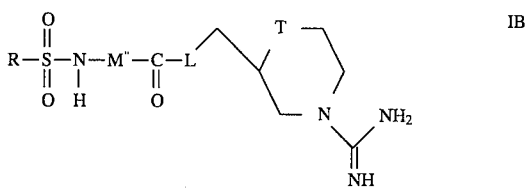

IB wherein

M" is a R"—COCH$_2$CH=, R'—(CO)$_{1-2}$NHCH$_2$CH=, benzyl-OCONHCH$_2$CH=, —CH$_2$[R'—(CO)$_{1-2}$NH] CH—, —CH$_2$(benzyl-OCONH)CH— or —CH(CO—Q")CH$_2$— group, and Q" is a tetra- to heptamethyleneimino group optionally interrupted by an O or S atom and optionally substituted by up to 2 substituents selected from the group $C_{1-4}$-alkyl, COOH, —COO—$C_{1-4}$-alkyl, —CH$_2$OH and —CH$_2$O-benzyl and R,R',R",L and T are as previously described.

Naphthyl, hydroxynaphthyl, 4-biphenyl, 2-anthryl, iodophenyl, nitrophenyl, benzyloxyphenyl, dimethoxyphenyl, 4-methoxy-2,3,6-trimethylphenyl, 2,4,6-triisopropylphenyl, carboxyphenyl, methoxycarbonylphenyl, benzyloxynaphthyl, phenylsulfonylphenyl, hexahydroazepinoylphenyl and t-butylphenyl are examples of the aryl group B.

3-Methyl-8-quinolyl, 5-(1-methyl-5-trifluoromethylpyrazol-3-yl)-2-thienyl and benzothienyl are examples of the heteroaryl group R.

3-Methyl-1,2,3,4-tetrahydro-8-quinolyl is an example of the heterocyclyl group R.

N-Dimethylaminonaphthylsulfonyl-aminomethylene is an example of a sulfonamide group —N(SO$_2$-R$^o$)—CH$_2$— as a meaning of —N(X)—M—.

More preferred compounds of formula I are, those in which X is H or —CH$_2$COOH.

When M is R'—(CH$_2$)$_{1-2}$CH=, examples of such groups are 3-indolylethylidene, 2,3-dioxo-1-indolinylethylidene, phenethylidene, 1,4-dioxo-5H-2,5-benzodiazepin-5-ylethylidene, (fluoro, chloro, iodo, cyano, nitro, amino, carboxy, $C_{1-4}$-alkoxycarbonyl or hydroxy)-phenethylidene, cyclohexylpropylidene, decalylethylidene, imidazolylethylidene, thienylethylidene, (methyl, bromo, fluoro or carboxymethyl)-3-indolylethylidene, naphthylethylidene, ethoxycarbonylcarbonylamino, methoxycarbonylethylcarbonylamino, benzyloxycarbonylethylcarbonylamino, ethoxycarbonylamino, benzoylcarbonylamino, carboxybenzoylamino, methoxyethoxyacetamido, acetamido, carboxycarbonylamino, carboxypropionylamino, tolylsulfonamido, iodophenylsulfonamido, carboxyphenylsulfonamido or ethoxycarbonylmethylamino)phenethylidene, oxobenzoxazolinethylidene or 5-bromo- or 5-methyl-2,3-dioxo-1-indolinylethylidene.

When M is (R' or R")COCH$_2$CH=, examples of such groups are hexahydroazepinoylethylidene, (methoxycarbonyl or carboxy)pyrrolidinoylethylidene, 3,4-dihydro-2(1H)-isoquinolinoylethylidene, (nitro, amino, iodo or formamido)benzoylethylidene, morpholinoethylidene, heptahydroazocinoylethylidene, (ethoxycarbonyl, acetoxymethyl, dimethylcarbamoyl, isobutyryloxymethyl or butyryloxymethyl)piperidinoylethylidene, 3-methoxycarbonyl-4-oxopiperidinoylethylidene or 4-acetoxy-3-ethoxycarbonylpiperidinoylethylidene.

When M is R'—(CO)$_{1-2}$NHCH$_2$CH=, examples of such groups are benzoylcarboxamidoethylidene, thienoylcarboxamidoethylidene, benzoylamidoethylidene or benzyloxycarboxamidoethylidene.

When M is —CH$_2$[R'—(CO)$_{1-2}$NH]CH—, examples of such groups are 2-(carboxybenzoylamido)ethylene, 2-(benzyloxybenzoylamido)ethylene, 2-(2-piperidinecarboxamido)ethylene, 2-(hydroxybenzoylamido)ethylene and 2-(aminobenzoylamido)ethylene.

When M is —CH(CO—Q)CH$_2$—, examples of such groups are 1-(benzylaminocarbonyl)ethylene, 1-(hexahydroazepinoyl)ethylene, 1-(morpholinoyl)ethylene, 1-(heptahydroazocinoyl)-ethylene, 1-[2-(benzyloxymethylmorpholinoyl)]ethylene, 1-[2-(hydroxymethylmorpholinoyl)]ethylene, 1-(2-ethoxycarbonyl-4

-methylpiperidinoyl)ethylene, 1-(2-carboxy-4-methylpiperidinoyl)ethylene and 1-(3-carboxyhexahydro-1,4-oxazepinoyl)ethylene.

In the above formulas R is preferably aryl, especially naphthyl or nitro- or iodophenyl, L is preferably NH and the asymmetric C atom in the piperidine or morpholine ring is preferably in the (S)-configuration.

Still more preferred compounds of formula I are those of the formula

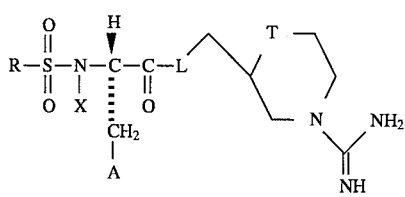   IC wherein A is aryl, aroyl or heterocyclyl, preferably phenyl, nitrophenyl, indolyl, 2,3-dioxo-1-indolinyl or aminobenzoyl.

The following are examples of preferred compounds:

(R)-N-[(RS)-1-Amidino-3-piperidinylmethyl]-α-(2-naphthylsulfonamido)- 2,3-dioxo-1-indolinepropionamide, (R)-N-[(RS)-1-amidino-3-piperidinylmethyl]-α-(2-naphthylsulfonamido)-o-nitrohydrocinnamamide, (R)-N-[(RS)-1-amidino-3-piperidinylmethyl]-α-(o-nitrobenzenesulfonamido)indole- 3-propionamide, (R)-N-[(S)-1-amidino-3-piperidinylmethyl]-α-(p-iodobenzenesulfonamido)indole- 3-propionamide, (R)-N-[(S)-1-amidino-3-piperidinylmethyl]-α-(p-iodobenzenesulfonamido)-p-nitrohydrocinnamamide, (R)-N-[(RS)-1-amidino-3-piperidinylmethyl]-3-(o-aminobenzoyl)-( 2-naphthylsulfonamido)propionamide, N-[(R)-α-[[(S)-1-amidino-3-piperidinyl]methylcarbamoyl]phenethyl]-N-(2-naphthylsulfonyl)glycine, (R)-N-[(S)-1-amidino-3-piperidinylmethyl]-1,2,3,4-tetrahydro- 2-(2-naphthylsulfonyl)-3-isoquinolinecarboxamide, (S)-N-[(RS)-1-amidino-3-piperidinylmethyl]hexahydro-β-(2 -naphthylsulfonamido)-1-oxo-1H-1-azepinebutyramide, (R)-N-[(S)-1-amidino-3-piperidinylmethyl]-α-(2-naphthylsulfonamido)- 2,3-dioxo-1-indolinepropionamide, 4'-[(R)-2-[[[(S)-1-amidino-3-piperidinyl]methyl]carbamoyl]-2-(2-naphthylsulfonamido)ethyl]oxanilic acid, (S)-N-[[(RS)-1-amidino-3-piperidinyl]methyl]hexahydro-β-2 -naphthylsulfonamido-γ-oxo-1(2H)-azocinebutyramide, (2RS,4R)-1-[N⁴-[[(S)-1-amidino-3-piperidinyl]methyl]-N²-(2 -naphthylsulfonyl)-L-asparaginyl]-4-methyl-2-piperidinecarboxylic acid, 4'-[(R)-2-[[[(S)-1-amidino-3-piperidinyl]methyl]carbamoyl]-2-(2-naphthylsulfonamido)ethyl]succinanilidic acid.

The above compounds can be manufactured by a) reacting an acid of the formula

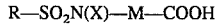   II with intermediary protection of a carboxy group present in the group X, R or M with an amine or alcohol of the formula

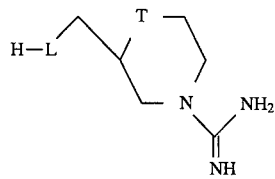   III or a salt thereof, or b) reacting a compound of the formula

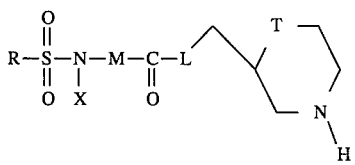   IV with an amidinating reagent, or c) reacting an amine of the formula

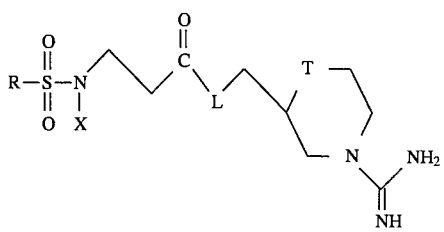   V with an acid of the formula R'—COOH or a functional derivative thereof, and d) if desired, functionally modifying a reactive group present in the group M in a compound of formula I, and e) if desired, converting a compound of formula I into a physiologically acceptable salt or converting a salt of a compound of formula I into the free acid or base.

Conveniently, the acid II in a solvent such as dimethylformamide (DMF) is reacted at room temperature in the presence of a base such as 4-ethylmorpholine or ethyldiisopropylamine with a salt of a compound of formula III, for example, a trifuloroacetate, bisulfite, nitrate, hydrochloride or hydroiodide, and with benzotriazol-1-yloxy-tris(dimethylamino)phosphonium hexa-fluorophosphate. A carboxy group protected, for example, as the t-butyl ester, which is present in group X, R or M, is thereby liberated.

In process variant b), the compound IV in a solvent such as DMF can be reacted in the presence of a base such as triethylamine with formamidinesulfonic acid or 3,5-dimethyl-1-pyrazoyl-formamidinium nitrate, conveniently at a temperature up to 50° C.

According to process variant c), the amine V can be reacted with an acid R'—COOH or a functional derivative, for example, an acid anhydride, in a solvent such as DMF in the presence of a base such as 4-ethylmorpholine at an elevated temperature, for example, up to 50° or 80° C.

The following can be mentioned as functional modifications in variant d):

1. The reduction of a nitroaryl group present in the group M to the aminoaryl group using Pd/C in a solvent such as ethanol;

2. the saponification of an ester group such as ethoxycarbonyl, for example, in ethanol or methanol using a base such as aqueous sodium hydroxide;

3. the saponification of an ester group such as benzyloxycarbonyl, for example, in ethanol using Pd/C;

4. the cleavage of a benzyl ether, for example, in ethanol using Pd/C in the presence of an acid such as hydrochloric acid or acetic acid.

The N-sulfonated amino acids II can be prepared by reacting a corresponding reactive sulfonic acid derivative such as the sulfonyl chloride R—SO₂Cl with the corresponding free amino acid HN(X)—M—COOH in the presence of a base such as an alkali metal hydroxide in a solvent such as an ether, for example, diethyl ether or dioxane, and water.

In a variant, an acid II can be prepared by oxidizing the corresponding alcohol

R—SO₂—N(X)—M—CH₂OH    VI for example, in a solvent such as acetone with an oxidizing agent such as Jones reagent. At the same time, a heteroyclyl radical R', such as 2-oxo-1-indolinyl, present in the group M of the alcohol VI is oxidized to 2,3-dioxo-1-indolinyl.

An alcohol VI can be prepared by reacting the corresponding α-amino alcohol HN(X)—M—CH₂OH in the presence of aqueous sodium hydroxide and sodium bicarbonate with the sulfonyl chloride R—SO₂Cl in dioxane.

An amino alcohol HN(X)—M—CH₂OH in which M is for example, a group —CH(CH₂—R')— can be prepared by cleaving a corresponding oxazolidine which is protected at the N atom and which is substituted in the 4-position by —CH₂—R', e.g. t-butyl (R)-2,2 -dimethyl-4-(CH₂—R')-3-oxazolidinecarboxylate, with hydrochloric acid in methanol.

The above oxazolidine can be prepared in a known manner, for example when R' is a heterocyclyl radical attached via a N atom, such as 2-oxo-1-indolinyl, by reacting the corresponding cyclic amine H—R' with t-butyl (S)-2,2-dimethyl-4-(p-tolylsulfonyloxymethyl)- 3-oxazolidinecarboxylate in the presence of a suspension of sodium hydride in DMF.

For the preparation of an amino acid II in which R is a hydroxyaryl radical, the corresponding sulfonyl chloride R—SO₂Cl in which the OH group is present in protected form, for example, as the acetoxy group, can firstly be reacted in acetone with the amino acid HN(X)—M—COOH in the presence of aqueous sodium hydroxide and then the protecting group, for example, acetyl, can be cleaved off with a solution of sodium hydroxide in water and methanol.

For the manufacture of a guanidine of formula, in which X is —CH₂COOH, the sulfonyl chloride R—SO₂Cl can first be reacted with a salt, for example, the p-toluenesulfonate, of an ester H₂N—M—COO-benzyl in a solvent such as methylene chloride in the presence of a base such as triethylamine. The resulting sulfonamide R—SO₂NH—M—COOC-benzyl is then reacted with t-butyl bromoacetate in a solvent such as THF at about −80° C. in the presence of butyllithium. Thereafter, the benzyl group is cleaved off selectively, for example, by catalytic hydrogenation with Pd/C in ethanol, from the resulting diester R—SO₂N(CH₂COO-t-butyl)—M—COO-benzyl As described above, in the reaction of the resulting acid with a compound of formula III, the carboxy group in the side-chain, which is protected as the t-butyl ester, is liberated.

The acid starting materials R—SO₂NHCH(CO—Q)—CH₂COOH can be prepared by a) reacting an aspartic acid derivative, for example, T-Butoxy-CONHCH(COOH)CH₂COO-benzyl with an amine H—Q corresponding to the group Q' in a solvent such as DMF in the presence of benzotriazol-1-yloxy-tris(dimethylamino)phosphonium hexafluorophosphate, b) reacting the resulting amide t-Butoxy-CONHCH(CO—Q)—CH₂COO-benzyl in a solvent such as ethyl acetate with an acid such as hydrochloric acid and then in dioxane with sodium hydroxide, sodium bicarbonate and a sulfonyl chloride R—SO₂Cl and c) cleaving the benzyl group in the resulting sulfonamide R—SO₂NHCH(CO—Q)—CH₂COO-benzyl in a solvent such as methanol using sodium hydroxide solution.

The compounds III, IV and V also form part of the invention. The piperidine derivatives of formula III can be prepared as described in Examples 1, 2 and 3 hereinafter from 3-picolylamine where L=NH or from 3-hydroxymethylpiperidine where L=O. Aminomethylmorpholine derivatives of formula III are obtained by reacting 2-aminomethyl-4-benzylmorpholine (J. Med. Chem. 33, 1990, 1406–1413) with di-t-butyl dicarbonate in dioxane, hydrogenating the resulting Boc-protected amine in ethanol in the presence of Pd/C to 2-(t-butoxycarbonylaminomethyl)morpholine and amidinating the latter. Hydroxymethylmorpholine derivatives of formula III can be prepared by amidinating 2-hydroxymethylmorpholine.

The compounds of formula IV are prepared by reacting the corresponding acid II with the compound of the formula

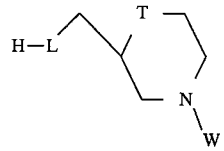

III' wherein W is a protecting group such as Boc or Z, for example, as described above for the reaction of the compound of formula II with a compound of formula III, followed by the cleavage of the protecting group, for example, using trifluoroacetic acid in methylene chloride, p-toluenesulfonic acid in acetonitrile or a solution of hydrogen chloride in ethyl acetate.

Alcohols of formula III' can be prepared as described in Example 3a) by introducing the protecting group at the N atom of 3-hydroxymethylpiperidine or as described in Example 19a) to c) starting from benzyloxymethyloxirane via 2-benzyloxymethylmorpholine and for example, Boc-protected 2-benzyloxymethylmorpholine. The resulting alcohol can be converted into the corresponding amine III' as described in Examples 6a) to d) and 19d) and e).

The amines V can be prepared by cleaving the benzyloxycarbonyl group in the corresponding compound I in which, for example, M is the group —CH₂(benzyl-OCO NH)CH— for example, in ethanol using Pd/C in the presence of hydrochloric acid.

The guanidines of formula I, their solvates and their salts inhibit not only platelet aggregation induced by thrombin, but also the thrombin-induced clotting of fibrinogen in blood plasma. The said compounds influence not only the platelet-induced, but also the plasmatic blood clotting. They therefore especially prevent the formation of hyaline thrombi and of platelet-rich thrombi and can be used in the control or prevention of illnesses such as thrombosis, stroke, cardiac infarct, inflammation and arteriosclerosis. Further, these compounds have an effect on tumor cells and prevent the formation of metastases. Accordingly, they can also be used as antitumor agents.

A differential inhibition of thrombin and other serine proteases by the above compounds is desirable in order to obtain compounds having as high a specificity as possible and at the same time to avoid possible side-effects. Alongside other tested serine proteases the ratio of the inhibition of trypsin to the inhibition of thrombin was taken as the general measurement for the specificity of a compound (q in the Table hereinafter), because trypsin as the most unspecific serine protease can be readily inhibited by the widest variety of inhibitors. In order for the inhibition of thrombin and trypsin to be directly comparable, not withstanding of the use of different substrates, the inhibition constant $K_i$ independent of substrate and enzyme concentration was determined as the measurement of the inhibition.

Specific chromogenic peptide substrates can be used to determine the inhibition of the catalytic activity of the above proteases. The inhibition of the amidolytic activity of thrombin and trypsin by the above guanidines was determined as described hereinafter.

The measurements were carried out on microtiter plates at room temperature. For this, in each well of the plate 150 µl of buffer (50 mM Tris, 100 mM NaCl, 0.1% polyethylene glycol; pH 7.8) were mixed with 50 µl of the inhibitor dissolved in DMSO and diluted in the buffer, and 25 µl of human thrombin (0.5 nM final conc.) were added. After incubation for 10 minutes, the reaction was started by the addition of chromogenic substrate S-2238 (H-D-Phe-Pip-Arg-paranitroaniline from Kabivitrum; 10 or 50 µm final conc.) and the hydrolysis of the substrate was followed spectrophotometrically on a kinetic microliter plate reader for 5 minutes. After graphical presentation of the inhibition curves, the Ki values were determined according to the method described in Biochem. J. 55, 1955, 170–171. The inhibition of trypsin was effected analogously, but using the substrate S-2251 (H-D-Val-Leu-Lys-paranitroaniline) in 200 and 750 µM final concentration.

The results will be evident from the following Table:

| Product of Example | 8 | 9 | 13a | 14i | 17b |
|---|---|---|---|---|---|
| $K_i$ (nM) Thrombin | 8.55 | 135 | 20.8 | 25 | 20.7 |
| $K_i$ (nM) Trypsin | 20075 | 168700 | 29200 | 38000 | 6300 |
| q | 2350 | 1250 | 1400 | 1520 | 304 |

| Product of Example | 17c | 17f | 17j | 18f |
|---|---|---|---|---|
| $K_i$ (nM) Thrombin | 58 | 41.3 | 26.1 | 16 |
| $K_i$ (nM) Trypsin | 10000 | 18300 | 14800 | 18850 |
| q | 172 | 455 | 565 | 1180 |

The guanidines of formula I have a low toxicity. Thus, the products of Example 8, 13a, 14i and 18f have an LD50 of 30–50 mg/kg in mice upon intravenous administration.

As mentioned earlier, medicaments containing a guanidine of formula I, a solvate or salt thereof are likewise objects of the present invention, as is a process for the manufacture of such medicaments which comprises bringing one or more of the said compounds and, where desired, one or more other therapeutically valuable substances into a galenical dosage form. The medicaments can be administered enterally, for example, orally in the form of tablets, coated tablets, dragees, hard and soft gelatine capsules, solutions, emulsions or suspensions, or rectally, for example, in the form of suppositories, or as a spray. The administration can, however, also be effected parenterally, for example, in the form of injection solutions.

For the manufacture of tablets, coated tablets, dragees and hard gelatin capsules, the active substance can be mixed with pharmaceutically inert, inorganic or organic excipients. Lactose, maize starch or derivatives thereof, talc, stearic acid or its salts can be used for example, as excipients for tablets, coated tablets, dragees and hard gelatin capsules. Suitable excipients for soft gelatin capsules are for example, vegetable oils, waxes, fats, semi-solid and liquid polyols; depending on the nature of the active sub-stance no excipients are, however, usually required in the case of soft gelatin capsules. Suitable excipients for the manufacture of solutions and syrups are for example, water, polyols, saccharose, invert sugar and glucose, suitable excipients for injection solutions are for example, water, alcohols, polyols, gycerol and vegetable oils and suitable excipients for suppositories are natural or hardened oils, waxes, fats, semi-liquid or liquid polyols. The pharmaceutical preparations can also contain preservatives, solubilizers, stabilizers, wetting agents, emulsifiers, sweeteners, colorants, flavorants, salts for varying the osmotic pressure, buffers, coating agents or antioxidants.

For the control or prevention of the illnesses mentioned above, the dosage of the active substance can vary within wide limits and will, of course, be fitted to the individual requirements in each particular case. In general, in the case of oral or parenteral administration a dosage of about 0.1 to 20 mg/kg, preferably of about 0.5 to 4 mg/kg, per day should be appropriate for adults, although the upper limit just given can also be exceeded when this is shown to be indicated.

EXAMPLE 1 a) A solution of 66.6 g of di-t-butyl dicarbonate in 200 ml of dioxan is added to a solution of 30 g of 3-picolylamine in 300 ml of dioxan so that the temperature does not exceed 25° C. The reaction mixture is stirred at room temperature for 3 hours and evaporated. After filtration over silica gel with ethyl acetate there are obtained 55.5 g of 3-t-butyloxycarbonyl-picolylamine.

b) 45.5 g of 3-t-butyloxycarbonyl-picolylamine are dissolved in 220 ml of methanol and catalytically hydrogenated with 4.6 g of ruthenium-on-aluminium (5%) at 60° C. under 100 bar or hydrogen. After filtration of the catalyst and evaporation of the solvent there are obtained 46 g of rac-3-t-butyloxycarbonylaminomethyl-piperidine.

c) 38.8 g of the product from b) are dissolved in 900 ml of DMF and treated with 74.5 ml of triethylamine. After the addition of 26.5 g of formamidinesulfonic acid the reaction mixture is stirred for 15 hours and subsequently filtered. The mother liquor is evaporated and the residue is taken up in water and extracted with ethyl acetate. The aqueous phase is evaporated and the product is evaporated azeotropically with ethanol, toluene and dichloro-ethane. The residue is suspended in ether and filtered. There are obtained 44.0 g of rac-3-t-butoxycarbonylaminomethyl- 1-amidinopiperidine hemisulphite, MS: 257 ($M^+$+1), 201, 157, 126, 96.

d) 27.8 g of the product from c) are dissolved in 70 ml of methylene chloride, treated with 70 ml of trifluoroacetic acid at 0° C. and stirred for 1 hour. The reaction mixture is evaporated and the residue is evaporated azeotropically with toluene and ethanol. There are obtained 27.6 g of rac-3-aminomethyl-1-amidinopiperidine sulphite, MS: 156 ($M^+$), 126 ($M^+$—$CH_2NH_2$), 69, 45.

EXAMPLE 2

A solution of 5.3 g of rac-3-hydroxymethylpiperidine in 100 ml of DMF is treated with 19 ml of triethylamine. After the addition of 6.8 g of formamidinesulphonic acid the reaction mixture is stirred for 15 hours. The suspension is filtered and the precipitate is washed with ether and dried. There are obtained 10.3 g of rac-3-hydroxymethyl-1-amidinopiperidine hemisulphite, MS: 158 (M+1), 143, 116, 102; m.p. 100° C.

EXAMPLE 3 a) A solution of 211.2 g of di-t-butyl dicarbonate in 500 ml of dioxan is added to a solution of 92.9 g of rac-3-hydroxymethylpiperidine in 1500 ml of dioxane so that the temperature does not exceed 25° C. The reaction mixture is stirred at room temperature for 15 hours and evaporated. The residue is suspended in 800 ml of hexane and filtered. There are obtained 120.7 g of rac-N-t-butyloxycarbonyl- 3-hydroxymethylpiperidine, m.p. 78° C.

b) A solution of 100 g of the product from a) in 4000 ml of methylene chloride is treated with 56.2 ml of pyridine and cooled to 0° C. 58.3 ml of butyryl chloride are added dropwise thereto so that the temperature does not exceed 10° C. The reaction mixture is subsequently stirred at room temperature for 15 hours. The suspension is filtered, the filtrate is evaporated and the residue is taken up in ethyl acetate. The organic phase is washed with aqueous 10% $CuSO_4$ solution, dried and evaporated. The residue is filtered through silica gel and eluted with hexane/ethyl acetate (8:2). There are obtained 119.7 g of t-butyl rac-3-(butyroxymethyl)- 1-piperidinecarboxylate.

c) 116.6 g of the product from b) are emulsified in 2 l of 0.1M sodium choride solution and 80 ml of sodium phosphate buffer, pH 7.0. The pH is adjusted to 7.0 with 1.0N sodium hydroxide solution and the reaction is started by the addition of 1.00 g of lipoprotein lipase produced from Pseudomonas fluorescens (Lipase P-30, Amano) in 10 ml of 0.1M sodium chloride solution. The pH is maintained at 7.0 by the addition of 2.0N sodium hydroxide solution while stirring. After 14 hours the reaction is terminated-by the addition of 500 ml of methylene chloride, the reaction mixture is extracted with methylene chloride and the organic phase is dried and evaporated. Chromatograpy of the residue over silica gel with hexane/ethyl acetate gives 36.6 g of t-butyl [S]-3-hydroxymethyl-1-piperidinecarboxylate, m.p. 89°–90° C., $[\alpha]_{365}^{25}=+53.5°$ (c=1.0, EtOH).

d) The 65.7 g of ester fraction from c) are emulsified in 1.15 l of 0.1M sodium chloride solution and 45 ml of 0.1M sodium phosphate buffer (pH 7.0) and treated with 0.50 g of Lipase P-30 in 5 ml of 0.1M sodium chloride solution. The pH is maintained at 7.0 by the addition of 2.0N sodium hydroxide solution while stirring. After 40 hours the reaction is terminated by the addition of 400 ml of methylene chloride, the reaction mixture is extracted with methylene chloride and the organic phase is dried and evaporated. Chromatography of the residue over silica gel o with hexane/ethyl acetate gives 49.5 g of t-butyl [R]-3-(butyryloxymethyl)- 1-piperidinecarboxylate. This is dissolved in 250 ml of ethanol, treated with 88 ml of 2N sodium hydroxide solution, stirred overnight and then evaporated. The residue is taken up in 200 ml of methylene chloride and washed with water, the aqueous phase is extracted with methylene chloride and the organic phase is dried and concentrated. Chromatography of the residue over silica gel with hexane/ethyl acetate gives 33.7 g of t-butyl [R]-3-hydroxymethyl-1-piperidinecarboxylate, $[\alpha]_{365}^{25}=-60.7°$ (c=1.0, EtOH).

e) A solution of 5.0 g of the product from d) in 20 ml of methylene chloride is cooled to 0° C. and treated with 15 ml of trifluoroacetic acid. After 2 hours the reaction mixture is evaporated and the residue is taken up in water and treated with sodium bicarbonate to pH 7.5. This aqueous phase is evaporated and the crystal mass is suspended in 100 ml of methylene chloride/ethanol (9:1). The salts are filtered off and the filtrate is evaporated. The residue is dissolved in 30 ml of DMF and treated with 9.7 ml of triethylamine. After the addition of 3.5 g of formamidinesulphonic acid the reaction mixture is stirred for 15 hours. The precipitate is filtered off and the solvent is evaporated. The residue is purified by reverse phase chromatography over silylated silica gel RP-18 with water. There are obtained 2.6 g of (R)-3-hydroxymethyl-1-amidinopiperidine hemisulphate, FAB-MS: 158 (M+1).

EXAMPLE 4

(S)-3-Hydroxymethyl-1-amidinopiperidine hemisulfate, FAB-MS: 158 (M+1), is manufactured from t-butyl [S]-3-hydroxymethyl- 1-piperidinecarboxylate analogously to Example 3e).

EXAMPLE 5

A solution of 1.5 g of N-(2-naphthylsulfonyl)-D-tryptophan in 30 ml of DMF is treated with 1.5 ml of ethylmorpholine. After the addition of 0.7 g of rac-3-aminomethyl-1-amidinopiperidine sulphite (Example 1)and 1.7 g of benzotriazol-1-yloxy-tris(dimethylamino)phosphonium hexafluorophosphate the reaction mixture is stirred for 15 hours. The solvent is evaporated and the residue is taken up in 50 ml of water and extracted with 100 ml of ethyl acetate. The ethyl acetate phase is washed with water, dried and evaporated. The crude material is purified on a RP-18 column with water/acetonitrile (0–30%). There is obtained 0.8 g of (R)-N-[(RS)-1-amidino-3-piperidinylmethyl]-α(2-naphthylsulfonamido)indole- 3-propionamide bisulfite, FAB-MS: 533 (M+H)⁺.

EXAMPLE 6 a) A solution of 5.0 g of t-butyl (S)-3-hydroxymethyl-1-piperidinecarboxylate (Example 3c) in 100 ml of pyridine is treated with 5.4 g of p-chlorosulphonyl chloride. The reaction mixture is stirred for 15 hours, evaporated, taken up in 200 ml of ethyl acetate and washed with water and aqueous 10% $CuSO_4$ solution. The organic phase is dried and evaporated. The residue is filtered over silica gel and eluted with hexane/ethyl acetate (8/2). There are obtained 6.5 g of t-butyl (S)-3-(p-chlorophenylsulfonyloxymethyl)- 1-piperidinecarboxylate.

b) A solution of the product from a) in 50 ml of DMF is treated with 3.25 g of sodium azide. The reaction mixture is stirred at 50° C. for 15 hours and evaporated. The residue is taken up in water and ether and washed with water. The ether phase is dried and evaporated. There are obtained 4.0 g of t-butyl (S)-3-azidomethyl- 1-piperidinecarboxylate.

c) A solution of the product from b) in 100 ml of ethanol is hydrogenated in the presence of 0.6 g of platinum oxide under 1 bar of hydrogen. Then, the reaction mixture is filtered over silica gel and eluted with methanol. There are obtained 3.4 g of t-butyl (R)-3-aminomethyl-1-piperidinecarboxylate, $[\alpha]_D^{25}=+23.0°$ (c=0.4, EtOH).

d) Using an identical process, from (R)-3-hydroxymethyl-1-piperidinecarboxylate there is obtained t-butyl (S)-3-aminomethyl- 1-piperidinecarboxylate, $[\alpha]_D^{25}=-17.7°$ (c=0.6 EtOH).

e) A solution of 1.5 g of N-(2-naphthylsulfonyl)-D-tryptophan in 50 ml of DMF is treated with 0.8 ml of ethyldiisopropylamine. After the addition of 1.0 g of the product from d) and 1.7 g of benzotriazol-1-yloxy-tris(dimethylamino)phosphonium hexafluorophosphate the reaction mixture is stirred for 15 hours. The solvent is evaporated and the residue is taken up in water and extracted with ethyl acetate. The ethyl acetate phase is washed with water, dried and evaporated. Chromatography over silica gel with ethyl acetate gives 2.3 g of (R)[(S)-1-(t-butoxycarbonyl)-3-piperidinylmethyl]-α-naphthylsulfonamidoindole-3-propionamide.

f) A solution of the product from e) in 10 ml of methylene chloride is treated at 0° C. with 3 ml of trifluoroacetic acid. The reaction mixture is stirred at 0° C. for 1 hour, evaporated and the residue is azeotroped with ethylene chloride. The residue is taken up in water and ethyl acetate, adjusted to pH 9 with 10% sodium carbonate and extracted. The organic phase is dried and evaporated. There are obtained 2.5 g of (R)-α-naphthylsulfonamido-N-[(S)-3-piperidinylmethyl]-indole-3-propionamide.

g) A solution of the product from f) in 50 ml of DMF is treated with 1.7 ml of triethylamine. After the addition of 0.7 g of formamidinesulphonic acid the reaction mixture is stirred for 15 hours. The solvent is evaporated and the residue is taken up in ethyl acetate and methanol. The organic phase is washed with water, dried and evaporated. Purification of the product on a RP-18 column with water/acetonitrile gives 1.85 g of (R)-N-[(S)-1-amidino-3-piperidinylmethyl]-α-(2-naphthylsulfonamido)-indole- 3-propionamide bisulfite, FAB-MS: 533 (M+H)$^+$.

EXAMPLE 7 a) A solution of 1.0 g of N-2-naphthylsulfonyl-(D)-tryptophan in 20 ml of DMF is treated with 0.5 ml of ethyldiisopropylamine. After the addition of 0.6 g of t-butyl (S)-3-hydroxymethyl-1-piperidinecarboxylate (Example 3c) and 1.1 g of benzotriazol-1-yloxy-tris(dimethylamino)phosphoniumhexafluorophosphate the reaction mixture is stirred for 15 hours. The solvent is evaporated and the residue is taken up in water and extracted with ethyl acetate. The ethyl acetate phase is washed with water, dried and evaporated. Chromatography over silica gel with ethyl acetate gives 1.0 g of N-(2-naphthylsulfonyl)-D-tryptophan (S)-1-t-butyoxycarbonyl- 3-piperidinylmethyl ester.

b) A solution of the product from a) in 10 ml of acetonitrile is treated with 0.9 g of p-toluenesulphonic acid. The reaction mixture is stirred for 15 hours. After evaporation the residue is taken up in ethyl acetate and washed with saturated sodium bicarbonate solution. The organic phase is dried and evaporated. Purification over a RP column with water/acetonitrile give 0.47 g of N-(2-naphthylsulfonyl)-D-tryptophan (S)-3-piperidinylmethyl ester.

c) A solution of the product from b) in 20 ml of DMF is treated with 0.4 ml of triethylamine. After the addition of 0.2 g of formamidinesulphonic acid the reaction mixture is stirred for 15 hours. The DMF is evaporated and the residue is taken up in ethyl acetate and washed with water. The organic phase is dried and evaporated. Purification on a RP column with water/acetonitrile gives 0.27 g of N-(2-naphthylsulfonyl)-D-tryptophan (S)-1 -amidino-3-piperidinylmethyl ester bisulfite, FAB-MS: 534 (M+1).

EXAMPLE 8 a) A solution of 10.7 g of t-butyl (R)-4-hydroxymethyl-2,2-dimethyl-3-oxazolidinecarboxylate (J. Org. Chem. 52, 1987, 2361–64) in 107 ml of pyridine is treated with 9.7 g of p-toluenesulphonyl chloride. The reaction mixture is stirred for 17 hours, then taken up in ethyl acetate and washed with water. After drying and evaporation the residue is purified over silica gel with hexane/ethyl acetate (3:1). There are obtained 15.1 g of t-butyl (S)-2,2-dimethyl-4-(p-tolylsulfonyloxymethyl)-3 -oxazolidinecarboxylate.

b) 4.6 g of of 2-indolinone are added to a suspension of 0.82 g of sodium hydride in 50 ml of DMF and the mixture is stirred for 90 minutes. Then, 6.6 g of the product from a) in 60 ml of DMF are added thereto and the reaction mixture is stirred at 50° C. overnight. After evaporation of the solvent the residue is taken up in ethyl acetate and washed with water. After drying and evaporation of the solvent the residue is purified over silica gel with ethyl acetate/hexane (1:4). There are obtained 2.5 g of t-butyl (R)-2,2-dimethyl-4-(2-oxo-1-indolinylmethyl)-3-oxazolidinecarboxylate.

c) A solution of 2.5 g of the product from b) in 30 ml of methanol is treated with 36 ml of 2N hydrochloric acid and stirred overnight. After evaporation of the solvent the residue is azeotroped with toluene. 1.56 g of the resulting 1-[(R)-2-amino-3-hydroxypropyl]-2-indolinone are dissolved in 2 equivalents of 1N sodium hydroxide solution. Thereto there are added 0.8 g of sodium bicarbonate in 8.1 ml of water and subsequently a solution of 1.46 g of 2-naphthylsulphonyl chloride in 28 ml of dioxan and the mixture is stirred overnight. The reaction mixture is poured into 200 ml of aqueous 5% potassium hydrogen sulphate/ 10% potassium sulphate and extracted with ethyl acetate. After washing the organic phase with water and drying the solvent is distilled off. The residue is purified over silica gel with methylene chloride/methanol (98/2). There are obtained 1.9 g of N-[(R)-2-hydroxy-1-(2-oxo-1-indolinylmethyl)ethyl]-2 -naphthylsulfonamide.

d) A solution of 1.82 of the product from c) in 70 ml of acetone is treated at 0° C. with 17.4 ml of Jones reagent and the mixture is stirred for 4 hours. The reaction mixture is poured on to ice and extracted with ethyl acetate. After washing the organic phase with water, drying and evaporation the product is purified over silica gel with methylene chloride/methanol (19:1) and 1% acetic acid. There are obtained 1.5 g of N-(2-naphthyl-sulfonyl)-3-(2,3 -dioxo-1-indolinyl)-D-alanine.

e) Analogously to Example 5, from the product of d) there is obtained (R)-N-[(RS)-1-amidino-3-piperidinylmethyl]-α-(2 -naphthylsulfonamido-2,3-dioxo-1-indolinepropionamide acetate (epimers 1:1), FAB-MS: 671 (M+H)$^+$.

EXAMPLE 9 a) 20 g of 2-naphthylsulphonyl chloride in 150 ml of ether are added to a solution of 7.3 g of (R)-phenylalanine in 120 ml of 1N sodium hydroxide solution. The reaction mixture is stirred for 15 hours and decanted. The aqueous phase is separated, washed with ether, acidified to pH 3 with HCl and extracted with ethyl acetate. The organic phase is dried and evaporated. The separated crystals are suspended in ether and filtered off. There are obtained 14.4 g of N-(2-naphthylsulfonyl)-3-phenyl-D-alanine, m.p. 146° C.

b) The following N-sulfonated amino acids are prepared using an identical process:

N-(2-Naphthylsulfonyl)-3-(p-chlorophenyl)-D-alanine, m.p. 154° C.

N-(2-naphthylsulfonyl)-3-(p-cyanophenyl)-D-alanine, m.p. 182° C.

N-(2-naphthylsulfonyl)-3-(p-nitrophenyl)-D-alanine, m.p. 218° C.

N-(2-naphthylsulfonyl)-3-benzyl-D-alanine, m.p. 138° C.
N-(2-naphthylsulfphonyl)-D-tryptophan, m.p. 167° C.
N-(2-biphenylsulfonyl)-D-tryptophan, m.p. 227°–230° C.
N-(2-anthrylsulfonyl)-D-tryptophan, m.p. 210° C.
N-(4-nitrophenylsulfonyl)-D-tryptophan, MS: M$^+$ 389
N-(2-nitrophenylsulfonyl)-D-tryptophan, m.p. 70°–80° C.
N-(3-nitrophenylsulfonyl)-D-tryptophan, m.p. 80°–84° C.
N-(4-benzyloxyphenylsulfonyl)-D-tryptophan, m.p. 193° C.
N-(3,4-dimethoxyphenylsulfonyl)-D-tryptophan, m.p. 182°–184° C.
N-(2,3,6-trimethyl-4-methoxyphenylsulfonyl)-D-tryptophan, MS: M$^+$ 416
N-(2,4,6-triisopropylphenylsulfonyl)-D-tryptophan, MS: M$^+$ 470
N-(2-naphthylsulfonyl)-5-methyltryptophan, m.p. 192° C.
(R)-2-(2-naphthylsulfonyl)-1,2,3,4-tetrahydro-3-iso-quinolinecarboxylic acid, m/e 322, 191, 176, 150, 127.

c) Analogously to Example 5, from the product of a) there is obtained (R)-N-[(RS)-1-amidino-3-piperidinylmethyl]-α-(2-naphthylsulfonamido)hydrocinnamide bisulfite (epimers 1:1), FAB-MS: 494 (M+H)$^+$.

EXAMPLE 10 a) 1.1 g of sodium hydride dispersion (60%) are suspended in 50 ml of DMF. 5.23 g of 4-methyl-3H-1,4-benzodiazepine-2,5(1H, 4H)-dione are added thereto so that the temperature does not exceed 35° C. and the mixture is stirred at room temperature for 90 minutes. Subsequently, a solution of 5.3 g of t-butyl (S)-2,2-dimethyl-4-(p-tolylsulfonyloxymethyl)-3-oxazolidinecaboxylate (Example 6a) in 50 ml of DMF is added thereto and the mixture is stirred at 50° C. overnight. The reaction mixture is evaporated and the residue is taken up in ethyl acetate, washed with water and dried. After evaporation of the solvent the residue is purified over silica gel with ethyl acetate/hexane (1:1). There are obtained 1.85 g of t-butyl (R)-(2,3,4,5-tetrahydro-4-methyl-2,5-dioxo-1H-1,4-benzodiazepin-1-ylmethyl)-2,2-dimethyl-3-oxazolidinecarboxylate.

b) A solution of the product from a) in 37 ml of methanol is treated with 23 ml of 2N hydrochloric acid. After stirring overnight the reaction mixture is evaporated. 1.37 g of the resulting 1-[(R)-2-amino-3-hydroxypropyl]-3,4-dihydro-4-methyl-2H-1,4-benzodiazepine-2,5(1H)-dione are dissolved in 15 ml of pyridine and treated with 2.08 g of 2-naphthylsulphonyl chloride. After 3 hours the reaction mixture is poured into 2N hydrochloric acid and extracted with ethyl acetate. The extracts are washed with water, dried and the solvent is evaporated. The residue is purified over silica gel with methylene chloride/methanol (97:3). 0.5 g of N-[(R)-1-hydroxymethyl-2-(2,3,4,5-tetrahydro-4-methyl-2,5-dioxo-1H-1,4-benzodiazepin-1-ylmethyl)ethyl]-2-naphthylsulfonamide is isolated.

c) A solution of 0.4 g of the product from b) in 12 ml of acetone is treated at 0° C. with 3 ml of Jones reagent. After 3 hours at room temperature the reaction mixture is poured on to ice and extracted with ethyl acetate. After washing with water and drying there is obtained, after evaporation, 0.4 g of N-(2-naphthylsulfonyl)-3-(2,3,4,5-tetrahydro-4-methyl-2,5-dioxo-1H-1,4-benzodiazepin-1-yl)-D-alanine.

d) Analogously to Example 5, from the product of c) there is obtained (R)-N-[(RS)-1-amidino-3-piperidinylmethyl]-1,2,3,4-tetrahydro-2-methyl-α-(2-naphthylsulfonamido)-1,4-dioxo-5H-2,5-benzodiazepine-5-propionamide (epimers 1:1), FAB-MS: 606 (M+H)$^+$.

EXAMPLE 11 a) A solution of 1.25 g of 6-acetoxynaphthyl-2-sulfonyl chloride (Monatsh. 49, 1928, 96) in 4.4 ml of acetone is added dropwise to a solution of 0.9 g of D-tryptophan in 4.8 ml of 1N NaOH and 4.8 ml of acetone and the pH is maintained at 9 by the addition of 1N NaOH. Then, the acetone is evaporated, the resulting suspension is acidified with 1N HCl and the product is extracted with ethyl acetate. The product is chromatographed on silica gel with ethyl acetate/acetone (1:1). The main fraction is o taken up in 8.8 ml of a methanolic solution of 0.5N NaOH and stirred for 17 hours. The solution is evaporated, treated with water and 1N HCl and extracted with ethyl acetate. Purification on silica gel with ethyl acetate/acetone (3:2) gives 0.54 g of N-(6-hydroxy-2-naphthylsulfonyl)-D-tryptophan, MS: M$^+$ 410, m/e 207, 130.

b) Analogously to Example 5 from the product of a) there is obtained (R)-N-[(RS)-1-amidino-3-piperidinylmethyl]-α-(6-hydroxy-2-naphthylsulfonamido)indole-3-propionamide hydrochloride (epimers 1:1), FAB-MS: 549 (M+H)$^+$.

EXAMPLE 12

The following compounds are manufactured analogously to Examples 5 and 9:

a) (R)-N-[(RS)-1-Amidino-3-piperidinylmethyl]-p-fluoro-α-(2-naphthylsulfonamido)hydrocinnamamide bisulfite (epimers 1:1), FAB-MS: 512 (M+H)$^+$.

b) (R)-N-[(RS)-1-Amidino-3-piperidinylmethyl]-p-chloro-α-(2-naphthylsulfonamido)hydrocinnamamide bisulfite (epimers 1:1), FAB-MS: 528 (M+H)$^+$.

c) (R)-N-[(RS)-1-Amidino-3-piperidinylmethyl]-p-cyano-α-(2-naphthylsulfonamido)hydrocinnamamide bisulfite (epimers 1:1), FAB-MS: 519 (M+H)$^+$.

d) (R)-N-[(RS)-1-Amidino-3-piperidinylmethyl]-α-(2-naphthylsulfonamido)-p-nitrohydrocinnamamide bisulfite (epimers 1:1), FAB-MS: 539 (M+H)$^+$.

e) (R)-p-Amino-N-[(RS)-1-amidino-3-piperidinylmethyl]-α-(2-naphthylsulfonamido)hydrocinnamamide bisulfite (epimers 1:1), FAB-MS: 509 (M+H)$^+$.

f) (R)-N-[(RS)-1-amidino-3-piperidinylmethyl]-3-(p-hydroxyphenyl)-2-(2-naphthylsulfonamido)propionamide bisulfite (epimers 1:1), FAB-MS: 510 (M+H)$^+$.

EXAMPLE 13

The following compounds are manufactured analogously to Examples 5 and 9:

a) (R)-N-[(RS)-1-Amidino-3-piperidinylmethyl]-α-(2-naphthylsulfonamido)-o-nitrohydrocinnamamide bisulfite (epimers 1:1), FAB-MS: 539 (M+H)$^+$.

b) (R)-N-[(RS)-1-Amidino-3-piperidinylmethyl]-α-(2-naphthylsulfonamido)cyclohexanepropionamide bisulfite (epimers 1:1), FAB-MS: 500 (M+H)$^+$.

c) (R)-N-[(RS)-1-Amidino-3-piperidinylmethyl]-2-(2-naphthylsulfonamido)-4-phenylbutyramide bisulfite (epimers 1:1), FAB-MS: 508 (M+H)$^+$.

d) (R)-N-[(RS)-1-Amidino-3-piperidinylmethyl]-α-(2-naphthylsulfonamido)cyclohexanebutyramide bisulfite (epimers 1:1), FAB-MS: 514 (M+H)$^+$.

e) (R)-N-[(RS)-1-Amidino-3-piperidinylmethyl]-α-(2-naphthylsulfonamido)-1-naphthylpropionamide bisulfite, FAB-MS: 586 (M+H)$^+$.

f) (R)-N-[(RS)-1-Amidino-3-piperidinylmethyl]-α-(2-naphthylsulfonamido)-2-naphthylpropionamide bisulfite (epimers 1:1), FAB-MS: 544 (M+H)$^+$.

g) (αR,2S,4aR and/or S,8aR and/or S)-N-[(RS)-1-amidino-3-piperidinylmethyl]decahydro-α-(2-naphthylsulfonamido)-2-naphthylpropionamide bisulfite (mixture of diastereomers), FAB-MS: 554 (M+H).

h)  (R)-N-[(RS)-1-Amidino-3-piperidinylmethyl]-α-(2-naphthylsulfonamido)-4-imidazolepropionamide bisulfite (epimers 1:1), FAB-MS: 484 (M+H)$^+$.

i)  (R)-N-[(RS)-1-Amidino-3-piperidinylmethyl]-α-(2-naphthylsulfonamido)-2-thienylpropionamide bisulfite (epimers 1:1), FAB-MS: 500 (M+H)$^+$.

EXAMPLE 14

The following compounds are manufactured analogously to Examples 5 and 11:

a)  (R)-N-[(RS)-1-Amidino-3-piperidinylmethyl]-α-(3-methyl-8-quinolinesulfonamido)indole-3-propionamide bisulfite (epimers 1:1), FAB-MS: 548 (M+H)$^+$.

b)  (R)-N-[(RS)-1-Amidino-3-piperidinylmethyl]-α-[(RS)-3-methyl-1,2,3,4-tetrahydro-8-quinolinesulfonamido]indole-3-propionamide bisulfite, (epimers 1:1), FAB-MS: 552 (M+H)$^+$.

c)  (R)-N-[(RS)-1-Amidino-3-piperidinylmethyl]-α-(4-biphenylsulfonamido)indole-3-propionamide hydrochloride (epimers 1:1), FAB-MS: 559 (M+H)$^+$.

d)  (R)-N-[(RS)-1-Amidino-3-piperidinylmethyl]-α-(2-anthrylsulfonamido)indole-3-propionamide hydrochloride (epimers 1:1), FAB-MS: 583 (M+H)$^+$.

e)  (R)-N-[(RS)-1-Amidino-3-piperidinylmethyl]-α-[5-(1-methyl-5-trifluoromethylpyrazol-3-yl)-2-thienylsulfonamido]-indole-3-propionamide bisulfite (epimers 1:1), FAB-MS: 637 (M+H)$^+$.

f)  (R)-N-[(RS)-1-Amidino-3-piperidinylmethyl]-α-(p-iodobenzenesulfonamido)indole-3-propionamide hydrochloride (epimers 1:1), FAB-MS: 609 (M+H)$^+$.

g)  (R)-N-[(RS)-1-Amidino-3-piperidinylmethyl]-α-(o-iodobenzenesulfonamido)indole-3-propionamide hydrochloride (epimers 1:1), FAB-MS: 608 (M+H)$^+$.

h)  (R)-N-[(RS)-1-Amidino-3-piperidinylmethyl]-α-(p-nitrobenzenesulfonamido)indole-3-propionamide hydrochloride (epimers 1:1), FAB-MS: 528 (M+H)$^+$.

i)  (R)-N-[(RS)-1-Amidino-3-piperidinylmethyl]-α-(o-nitrobenzenesulfonamido)indole-3-propionamide hydrochloride (epimers 1:1), FAB-MS: 528 (M+H)$^+$.

j)  (R)-N-[(RS)-1-Amidino-3-piperidinylmethyl]-α-(m-nitrobenzenesulfonamido)indole-3-propionamide hydrochloride (epimers 1:1), FAB-MS: 528 (M+H)$^+$.

k)  (R)-N-[(RS)-1-Amidino-3-piperidinylmethyl]-α-(p-benzyloxybenzenesulfonamido)indole-3-propionamide hydrochloride (epimers 1:1), FAB-MS: 589 (M+H)$^+$.

l)  (R)-N-[(RS)-1-Amidino-3-piperidinylmethyl]-α-(3,4-dimethoxybenzenesulfonamido)indole-3-propionamide hydrochloride (epimers 1:1), FAB-MS: 543 (M+H)$^+$.

m)  (R)-N-[(RS)-1-Amidino-3-piperidinylmethyl]-α-(4-methoxy-2,3,6-trimethylbenzenesulfonamido)indole-3-propionamide hydrochloride (epimers 1:1), FAB-MS: 555 (M+H)$^+$.

n)  (R)-N-[(RS)-1-Amidino-3-piperidinylmethyl]-α-(2,4,6-triisopropylbenzenesulfonamido)indole-3-propionamide hydrochloride (epimers 1:1), FAB-MS: 609 (M+H)$^+$.

EXAMPLE 15

The following compounds are manufactured analogously to Example 5:

a)  (RS)-N-[(RS)-1-Amidino-3-piperidinylmethyl]-5-methyl-α-(2-naphthylsulfonamido)indole-3-propionamide bisulfite, FAB-MS: 547 (M+H)$^+$.

b)  (RS)-N-[(RS)-1-Amidino-3-piperidinylmethyl]-5-fluoro-α-(2-naphthylsulfonamido)indole-3-propionamide bisulfite, FAB-MS: 551 (M+H)$^+$.

c)  3-[(R)-2-[(RS)-1-Amidino-3-piperidinylmethylcarbamoyl]-2-(2-naphthylsulfonamido)ethyl]indole-1-acetic acid bisulfite (epimers 1:1), FAB-MS: 591 (M+H)$^+$.

EXAMPLE 16

Analogously to Example 6 and, respectively, Example 7 there are obtained:

a)  (R)-N-[(R)-1-Amidino-3-piperidinylmethyl]-α-(2-naphthylsulfonamido)indole-3-propionamide bisulfite, FAB-MS: 533 (M+H)$^+$, and, respectively, b)  N-(2-naphthylsulfonyl)-D-tryptophan (R)-1-amidino-3-piperidinylmethyl ester p-toluenesulfonate (1:1), FAB-MS: 534 (M+H)$^+$.

EXAMPLE 17

The following compounds are obtained analogously to Examples 6 and 7:

a)  (R)-N-[(R)-1-Amidino-3-piperidinylmethyl]-α-(p-iodobenzenesulfonamido)indole-3-propionamide p-toluenesulfonate (1:1), FAB-MS: 609 (M+H)$^+$.

b)  (R)-N-[(S)-1-Amidino-3-piperidinylmethyl]-α-(p-iodobenzenesulfonamido)indole-3-propionamide p-toluenesulfonate (1:1), FAB-MS: 609 (M+H)$^+$.

c)  N-(p-Iodophenylsulfonyl)-D-tryptophan (R)-1-amidino-3-piperidinylmethyl ester p-toluenesulfonate (1:1), FAB-MS: 609 (M+H)$^+$.

d)  N-(p-Iodophenysulfonyl)-D-tryptophan (S)-1-amidino-3-piperidinylmethyl ester p-toluenesulfonate (1:1), FAB-MS: 610 (M+H)$^+$.

e)  (R)-N-[(R)-1-Amidino-3-piperidinylmethyl]-α-(p-iodobenzenesulfonamido)-2-naphthylpropionamide p-toluenesulfonate (1:1), FAB-MS: 620 (M+H)$^+$.

f)  (R)-N-[(S)-1-Amidino-3-piperidinylmethyl]-α-(p-iodobenzenesulfonamido)-2-naphthylpropionamide p-toluenesulfonate (1:1), FAB-MS: 620 (M+H)$^+$.

g)  N-(p-Iodophenylsulfonyl)-3-(2-naphthyl)-D-alanine (R)-1-amidino-3-piperidinylmethyl ester p-toluenesulfonate (1:1), FAB-MS: 621 (M+H)$^+$.

h)  N-(p-Iodophenylsulfonyl)-3-(2-naphthyl)-D-alanine (S)-1-amidino-3-piperidinylmethyl ester p-toluenesulfonate (1:1), FAB-MS: 621 (M+H)$^+$.

i)  (R)-N-[(R)-1-Amidino-3-piperidinylmethyl]-α-(p-iodobenzenesulfonamido)-p-nitrohydrocinnamamide bisulfite (2:1), FAB-MS: 615 (M+H)$^+$.

j)  (R)-N-[(S)-1-Amidino-3-piperidinylmethyl]-α-(p-iodobenzenesulfonamido)-p-nitrohydrocinnamamide p-toluenesulfonate (1:1), FAB-MS: 615 (M+H)$^+$.

k)  N-(p-Iodophenylsulfonyl)-3-(p-nitrophenyl)-D-alanine (R)-1-amidino-3-piperidinylmethyl ester p-toluenesulfonate (1:1), FAB-MS: 616 (M+H)$^+$.

l)  N-(p-Iodophenylsulfonyl)-3-(p-nitrophenyl)-D-alanine (S)-1-amidino-3-piperidinylmethyl ester p-toluenesulfonate (1:1), FAB-MS: 616 (M+H)$^+$.

EXAMPLE 18

The following compounds are manufactured analogously to Example 5:

a) (R)-N-[(RS)-1-Amidino-3-piperidinylmethyl]hexahydro-α-2 -naphthylsulfonamido-γ-oxo-1H-azepine-1-butyramide bisulfite (epimers 1:1), FAB-MS: 543 (M+H)$^+$.

b) 1-[(R)-23-[(RS)-1-Amidino-3-piperidinylmethylcarbamoyl]3-(2-naphthylsulfonamido)propionyl]-L-proline methyl ester (epimers 1:1), FAB-MS: 573 (M+H)$^+$.

c) 1-[(R)-3-[(RS)-1-Amidino-3-piperidinylmethylcarbamoyl]3-(2-naphthylsulfonamido)propionyl]-L-proline (epimers 1:1), FAB-MS: 559 (M+H)$^+$.

d) (R)-N-[(RS)-1-Amidino-3-piperidinylmethyl]-3,4-dihydro-α-(2-naphthylsulfonamido)-γ-oxo-2(1H)-isoquinolinebutyramide (epimers 1:1), FAB-MS: 577 (M+H)$^+$.

e) (RS)-N-[(RS)-1-Amidino-3-piperidinylmethyl]-2-(2 -naphthylsulfonamido)-3-(o-nitrobenzoyl)propionamide bisulfite, FAB-MS: 567 (M+H)$^+$.

f) (R)-N-[(RS)-1-Amidino-3-piperidinylmethyl]-3-(o-aminobenzoyl)- 2-(naphthylsulfonamido)propionamide (epimers 1:1), FAB-MS: 537 (M+H)$^+$.

g) (R)-N-[(RS)-1-Amidino-3-piperidinylmethyl]-3-anthraniloyl- 2-(p-iodobenzenesulfonamido)propionamide trifluoroacetate (epimers 1:1), FAB-MS: 613 (M+H)$^+$.

h) (R)-N-[(RS)-1-Amidino-3-piperidinylmethyl]-3-(o-formamidobenzoyl)-α-(2-naphthylsulfonamido)propionamide acetate (epimers 1:1), FAB-MS: 565 (M+H)$^+$.

EXAMPLE 19 a) 199 g of 2-aminoethyl hydrogen sulfate are added to 164 ml of 70% sodium hydroxide solution, the solution is heated to 50° C. and added dropwise to a solution of (RS)-benzyloxymethyloxirane in 280 ml of methanol. After 1 hour at 50° C. a further 280 ml of 70% sodium hydroxide solution are added thereto and the solution is stirred overnight. Then, the reaction mixture is poured on to ice and extracted with toluene. The organic phase is washed with water, dried and evaporated. After distillation there are obtained 26.8 g of rac-2-benzyloxymethylmorpholine, MS: M$^+$ −91=116 (benzyl).

b) A solution of 31.0 g of di-t-butyl dicarbonate in 287 ml of dioxane is added 26.8 g of the product from a) in 287 ml of dioxane and the reaction mixture is stirred overnight. After evaporation of the solvent and chromatography of the residue on silica gel with ethyl acetate/hexane there are obtained 15 g of t-butyl rac-2-benzyloxymethyl-4-morpholinecarboxylate, MS: M$^+$ −515=251 (isobutylene).

c) A solution of 15 g of the product from b) in 300 ml of ethanol is hydrogenated in the presence of 1.5 g of Pd/C under normal conditions and, after filtration and evaporation of the solvent, there is obtained quantitatively t-butyl rac-2-hydroxymethyl- 4-morpholinecarboxylate, MS: M$^+$=217.

d) A solution of 8.8 g of the product from c) in 44 ml of pyridine is treated with 9.4 g of p-chlorobenzenesulfonyl chloride. After stirring for 5 hours the reaction mixture is evaporated, the residue is taken up in ethyl acetate and washed with 10% copper sulphate solution. After drying the organic phase, evaporation of the solvent and chromatography of the residue on silica gel with ethyl acetate/hexane there are obtained 14.7 g of t-butyl rac-2 -(p-chlorophenylsulfonyloxymethyl)-4-morpholinecarboxylate, MS: 392 (M+H)$^+$.

e) 7.3 g of sodium azide are added to a solution of 14.7 g of the product from d) in 91 ml of DMF. After stirring at 50° C. for 24 hours the reaction mixture is poured on to ice and extracted with ether. The organic phase is washed with water, dried and evaporated. 8.1 g of t-butyl rac-2-azidomethyl-4-morpholinecarboxylate are obtained.

f) A solution of 8.1 g of the product from e) in 92 ml of ethanol is hydrogenated in the presence of 0.8 g of platinum oxide for 4 hours under normal conditions and 6.5 g of t-butyl rac-2 -aminomethyl-4-morpholinecarboxylate, (MS: M+H)$^+$ −56=159 (isobutylene) are isolated.

g) A solution of 3.0 g of N-(2-naphthylsulfonyl)-D-tryptophan (Example 9) in 35 ml of DMF is treated with 1.2 ml of 4-ethylmorpholine and with 3.4 g of benzotriazol-1-yloxy-tris(dimethylamino)phosphonium hexafluorophosphate. A solution of 2.0 g of the product from f) in 2 ml of DMF is added thereto and the solution is stirred overnight. Then, the solvent is distilled off and the residue is taken up in ethyl acetate and washed with water. After drying, evaporation of the solvent and chromatography of the residue on silica gel with ethyl acetate there are obtained 4.5 g of t-butyl (RS)-2-N-(2-naphthylsulfonyl)-D-tryptophylaminomethyl-4-morpholinecarboxylate, MS: (M+H)$^+$ −56=537 (isobutylene).

h) A solution of 2 g of the product from g) in 20 ml of ethyl acetate is treated with 20 ml of a 4 molar solution of HCl in ethyl acetate. After stirring the solution is evaporated to dryness. The residue is dissolved in 20 ml of DMF, treated with 1.4 ml of triethylamine and 0.5 g of formamidinesulphonic acid and stirred at room temperature for 17 hours. Then, the solvent is evaporated, the residue is taken up in 50 ml of ethyl acetate and 10 ml of methanol and this solution is washed with water. After drying the organic phase, evaporation of the solvent and chromatography of the residue on a RP column (alkylsilylated silica gel) with water/acetonitrile there is obtained 0.1 g of (R)-N-[(RS)-4-amidino-2-morpholinylmethyl]-α-(2-naphthylsulfonamido)indole-3-propionamide bisulfite, MS: 535 (M+H)$^+$.

EXAMPLE 20

Analogously to Example 19g) and h), from t-butyl rac-2 -hydroxymethyl-4-morpholinecarboxylate (Example 19c) and N(-2-naphthylsulfonyl)-D-tryptophan there is obtained N-(2 -naphthylsulfonyl)-D-tryptophan (RS)-4-amidino-2-morpholinylmethyl ester bisulfite, MS: 536 (M+H)$^+$.

EXAMPLE 21

Analogously to Example 19 there are obtained a) (R)-N-[(RS)-4-amidino-2-morpholinylmethyl]-α-(2 -naphthylsulfonyl)-p-nitrohydrocinnamamide bisulfite, MS: 541 (M+H)$^+$ b) (R)-N-[(RS)-4-amidino-2-morpholinylmethyl]-α-(2 -naphthylsulfonamido)-2-thienylpropionamide bisulfite, MS: 502 (M+H)$^+$ c) (R)-N-[(RS)-4-amidino-2-morpholinylmethyl]-3-(o-aminobenzoyl)- 2-(2-naphthylsulfonamido)propionamide bisulfite, MS: 539 (M+H)$^+$.

EXAMPLE 22 a) A solution of 10 g of (D)-phenylalanine benzyl ester p-toluenesulphonate in 150 ml of methylene chloride is treated with 8.2 ml of triethylamine and cooled to 0° C.

5.8 g of 2-naphthylsulphonyl chloride are added thereto and the mixture is stirred at room temperature for 12 hours. The reaction mixture is evaporated, the residue is taken up in 200 ml of ethyl acetate, the precipitated triethylammonium chloride salt is filtered off under suction and the mother liquor is washed with water. After evaporation of the organic phase and crystallization from hexane there are obtained 9.7 g of N-(2-naphthylsulfonyl)-3-phenyl-D-alanine benzyl ester, m.p. 107° C.

b) A solution of 3 g of the product from a) in 40 ml of THF is treated at −80° C. with 5 ml of 1.6M butyllithium in hexane and then with 1.2 ml of t-butyl bromoacetate. After stirring at room temperature for 2 hours the reaction mixture is taken up in 200 ml of ethyl acetate, washed with water and the organic phase is evaporated. The product is purified over silica gel with hexane/ethyl acetate (9:1). There are obtained 1.35 g of N-(t-butoxycarbonylmethyl)-N-( 2-naphthylsulfonyl)-3-phenyl-D-alanine benzyl ester, NMR (CDCl$_3$) 1.45 (s, 9H, t-butyl).

c) A solution of 1.35 g of the product from b) in 50 ml of ethanol is hydrogenated in the presence of 0.3 g of Pd/C. After evaporating the reaction mixture and azeotroping with toluene there is obtained 0.95 g of N-(t-butoxycarbonylmethyl)-N-(2 -naphthylsulfonyl)-3-phenyl-D-alanine.

d) Analogously to Example 5 there is obtained N-[(R)-α-[[(S)-1 -amidino-3-piperidinyl]methylcarbamoyl]phenethyl]-N-(2 -naphthylsulfonyl)glycine, FAB-MS: 552 (M+H)$^+$.

EXAMPLE 23 a) 13.7 g of benzotriazol-1-yloxy-tris(dimethylamino) phosphonium hexafluorophosphate and 16.9 ml of benzylamine are added to a solution of 10.0 g of N-Boc-L-aspartic acid β-benzyl ester in 200 ml of DMF and the reaction mixture is stirred at room temperature overnight. Then, the solvent is evaporated and the residue is taken up in ethyl acetate and washed with water. After drying, evaporation and chromatography on silica gel with ethyl acetate/hexane (1:4) there are obtained 5.4 g of benzyl (S)-3-(1,1 -dimethylethoxycarbonylamino)-4-benzylamino-4-oxo-butyrate.

b) A solution of 2.0 g of the product from a) in 10 ml of ethyl acetate is treated with 10 ml of a 4 molar solution of HCl in ethyl acetate. After stirring for 3 hours the mixture is evaporated and the residue is suspended in 30 ml of dioxan. 5 ml of 1N sodium hydroxide solution, 0.8 g of sodium bicarbonate, 20 ml of water and then a solution of 1.1 g of 2-naphthylsulphonyl chloride in 15 ml of dioxan are added thereto and the mixture is stirred at room temperature overnight. The reaction mixture is poured into 5% potassium hydrogen sulphate/10% potassium sulphate solution and extracted with ethyl acetate. After drying and evaporating the organic phase the residue is recrystallized from ethyl acetate/hexane. 1.8 g of (S)-2-benzylcarbamoyl-N-(2-naphthylsulfonyl)-β-alanine benzyl ester are obtained.

c) A solution of 1.0 g of the product from b) in 20 ml of methanol is treated with 2 ml of 1N sodium hydroxide solution and stirred at room temperature overnight. The mixture is acidified, extracted with ethyl acetate and, after evaporation, the residue obtained is crystallized from methanol/methylene chloride/hexane. 0.3 g of (S)-2-benzycarbamoyl-N-(2-naphthylsulfonyl)-β-alanine is obtained.

d) Analogously to Example 5 there is obtained (S)-N-[(RS)-1 -amidino-3-piperidinylmethyl]-3-benzylcarbamoyl-3-(2-naphthylsulfonamido)propionamide trifluoroacetate (epimers 1:1), FAB-MS: 5:51 (M+H)$^+$.

EXAMPLE 24

Analogously to Example 23, via (R)-2-benzylcarbamoyl-N-(2-naphthylsulfonyl)-β-alanine there is obtained (R)-N-[(RS)-β-amidino-3-piperidinylmethyl]-3-benzylcarbamoyl-3-(2-naphthylsulfonamido)propionamide hydrochloride, FAB-MS: 551 (M+H)$^+$.

EXAMPLE 25

Analogously to Example 23, using hexamethyleneimine in place of benzylamine there is obtained (S)-N-[(RS)-1-amidino-3-piperidinylmethyl]hexahydro-β-(2-naphthylsulfonamido)-γ-oxo- 1H-1-azepinebutyramide trifluoroacetate, FAB-MS: 543 (M+H)$^+$.

EXAMPLE 26

Analogously to Example 6 there is obtained (R)-N-[(S)-1 -amidino-3-piperidinylmethyl]1,2,3,4-tetrahydro-2-(2-naphthylsulfonyl)- 3-isoquinolinecarboxamide hydrochloride, FAB-MS: 506 (M+H)$^+$.

EXAMPLE 27

Analogously to Examples 5 and 9 there is obtained methyl o-[(R)-α-[(RS)-1-amidino-3-piperidinylmethylcarbamoyl]-p-nitrophenethylsulfamoyl]benzoate, FAB-MS: 547 (M+H)$^+$.

EXAMPLE 28

Analogously to Examples 5 and 9 there is obtained (RS)-N-[[(RS)-1-amidino-3-piperidinyl]methyl]-5-bromo-α-2-naphthylsulfonamidoindole- 3-propionamide sulfite, FAB-MS: 611 (M+H)$^+$.

EXAMPLE 29

The following compounds are manufactured analogously to Examples 6 and 9:

a)  (R)-N-[[(RS)-1-Amidino-3-piperidinyl]methyl]-p-iodo-α-2-naphthylsulfonamidohydrocinnamide p-toluenesulfonate, FAB-MS: 620 (M+H)$^+$.

b)  (R)-N-[[(S)-1-Amidino-3-piperidinyl]methyl]-α-2-naphthylsulfonamido-p-nitrohydrocinnamide p-toluenesulfonate, FAB-MS: 539 (M+H)$^+$.

EXAMPLE 30 a) A solution of 30.1 g of t-butyl (R)-4-hydroxymethyl-2,2 -dimethyl-3-oxazolidinecarboxylate t-butyl ester in 400 ml methylene chloride, cooled to 0°, is treated with 27.2 ml of triethylamine. After the addition of 12.1 ml of methanesulfonyl chloride at 0° the reaction mixture is stirred for 1 hour. The salts are filtered off, the filtrate is evaporated and the product is recrystallized from hexane. There are obtained 32.7 g of t-butyl (S)-2,2-dimethyl-4-(methanesulfonyloxymethyl)-3-oxazolidinecarboxylate, H$^1$-NMR (CDCl$_3$): 1.48, s, 9H, t-butyl; 3.04, s, 3H, mesyl.

b) A solution of 29.1 g of the product from a) in 200 ml of DMF is treated with 24.5 g of sodium azide. The suspension is heated to 50° and stirred for 24 hours. The salts are then filtered off and the filtrate is evaporated. The crude product is dissolved in 400 ml of ethyl acetate and washed with water. The organic phase is dried and evaporated. There are obtained 20.2 g of t-butyl (R)-2,2-dimethyl-4-(azidomethyl)-3-oxazolidinecarboxylate, IR (CHCl$_3$) 2140 cm$^{-1}$ (azide-band).

c) A solution of 20.2 g of the product from b) in 400 ml of dioxane is treated with 4 g of platinium oxide. The reaction mixture is hydrogenated at room temperature and normal pressure. After filtration and evaporation of the filtrate there are obtained 17.9 g of t-butyl (R)-2-2-dimethyl-4-(amino-methyl)-3-oxazolidinecarboxylate.

d) A solution of the product from c) in 300 ml of methylene chloride is treated at 0° with 19.9 ml of Hünig base (ethyldiisopropylamine) and 12.2 ml of benzyl chloroformate. After stirring the reaction mixture is evaporated and the crude product is dissolved in 400 ml of ethyl acetate and washed with 100 ml of water. The organic phase is dried and evaporated and the crude material is purified on silica gel with ethyl acetate/hexane (1:9). There are obtained 26.4 g of t-butyl (R)-2,2-dimethyl-4-(carbobenzoxyaminomethyl)-3-oxazolidinecarboxylate.

e) A solution of the product from d) in 300 ml of methanol is treated with 36.2 ml of 2N HCl. After 24 hours the solution is evaporated and the residue is dissolved in 400 ml of dioxan and treated with 72.43 ml of 1N NaOH. After the addition of 30.4 g of sodium bicarbonate the suspension is treated with a solution of 24.6 g of 2-naphthylsulphonyl chloride in 100 ml of dioxan. The suspension is stirred for 15 hours, the reaction mixture is then filtered, evaporated, taken up in ethyl acetate, washed with water and dried. The organic phase is evaporated and the crude product is purified on silica gel with ethyl acetate/hexane (3:7). There are obtained 25.85 g of benzyl [(R)-3-hydroxy-2-(2-naphthylsulfonamido)propyl]carbamidate, MS: 415 $(M+H)^+$, 371 ($-CO_2$), 347, 325, 281, 269, 225, 191, 135.

f) After the addition of 1 g of 10% Pd/C a solution of 5 g of the product from e) in 100 ml of ethanol is hydrogenated at room temperature under normal pressure for 24 hours. The catalyst is filtered off and washed with methanol. After evaporation there are obtained 2.8 g of N-[(R)-2-amino-1-hydroxymethyl)ethyl]-2-naphthylsulfonamide, MS: 281 $(M+H)^+$ 251, 250, 221, 191, 128, 127, 60.

g) A solution of 1.3 g of the product from f) in 500 ml of DMF is treated with 0.83 g of phenylglyoxalic acid and 0.9 ml of Hünig base. After the addition of 2.0 g of benzotriazol-1-yloxytris(dimethylamino)phosphonium hexafluorophosphate the reaction mixture is stirred for 5 hours. The solvent is evaporated and the crude product is purified on silica gel with hexane/ethyl acetate (1:1). There are obtained 1.4 g of N-[(R)-3 -hydroxy-2-(2-naphthylsulfonamido)propyl]-2-phenylglyoxylamide.

h) A solution of 0.42 g of the product from g) in 30 ml of acetone is treated at 0° with 3.5 ml of Jones reagent (2.67 mg of $CrO_3$ in sulphuric acid). The mixture is stirred for 1 hour, poured on to ice-water and extracted with ethyl acetate. The organic phase is dried and evaporated. There is obtained 0.44 g of (R)-2 -(2-naphthylsulfonamido)-3-(2-phenylglyoxylamido)propionic acid, FAB-MS: 427 $(M+1)^+$.

i) Analogously to Example 5, from the product of h) there is obtained (R)-N-[[(S)-1-amidino-3-piperidinyl]methyl]-2-naphthylsulfonamido-3-(2 -phenylglyoxylamido)propionamide p-toluenesulfonate. FAB-MS: 565 $(M+H)^+$.

EXAMPLE 31

Analogously to Examples 5 and 9 there are obtained a) via N-[(6-benzyloxy-2-naphthyl)sulfonyl]-D-tryptophan, FAB-MS: 394 $(M+H)^+$,
the (R)-N-[[(RS)-1-amidino-3-piperidinyl]methyl]-α-(6 -benzyloxy-2-naphthylsulfonamido)indole-3-propionamide hydrochloride, FAB-MS: 639 $(M^+)$, b) via N-(1-naphthylsulphonyl)-D-tryptophan, FAB-MS: 394 $(M+H)^+$,
the (R)-N-[[(RS)-1-amidino-3-piperidinyl]methyl]-α-(1 -naphthylsulfonamido)indole-3-propionamide hydrochloride, FAB-MS: 533 $(M+H)^+$, c) via N-(2-naphthylsulfonyl)-3-(m-nitrophenyl)-DL-alanine, MS: 400 $(M^+)$,
the (RS)-N-[[(RS)-1-amidino-3-piperidinyl]methyl]-α-[2-naphthylsulfonamido]-m-nitrohydrocinnamamide hydrochloride, FAB-MS: 539 $(M+H)^+$.

EXAMPLE 32 a) 0.36 g of sodium hydrogen carbonate and a solution of 0.50 g of methyl p-(chlorosulfonyl)benzoate in 10 ml of ether are acided to a solution of 0.71 g of of D-tryptophan in 4.8 ml of water and 2.13 ml of 1N NaOH. The resulting suspension is stirred for 22 hours. The sodium salt of N-[[p-(methoxycarbonyl)phenyl]sulfonyl]-D-tryptophan is filtered under suction and rinsed with water (0.52 g), MS: 400 $(M-Na)^-$. 0.38 g of product as the free acid is isolated from the mother liquor after acidification with citric acid.

b) Analogously to Examples 5 and 11, from the acid from a) there is obtained methyl p-[[(R)-1-[[[(RS)-1-amidino-3-piperidinyl]methyl]carbamoyl]-2-indol-3-ylethyl]sulfamoyl]benzoate hydrochloride, FAB-MS: 541 $(M+H)^+$.

EXAMPLE 33

Analogously to Example 31 there is obtained (RS)-N-[[(S)-1 -amidino-3-piperidinyl]methyl]-α-2-naphthylsulfonamido-m-nitrohydrocinnamamide hydrochloride, FAB-MS: 539 $(M+H)^+$.

EXAMPLE 34

A solution of 0.15 g of (RS)-N-[[(S)-1-amidino-3-piperidinyl]methyl]-α-2-naphthylsulfonamido-m-nitrohydrocinnamamide hydrochloride (Example 33) in 50 ml of ethanol is treated with 0.12 g of 10% Pd/C and hydrogenated at room temperature under normal pressure. The reaction solution is filtered and evaporated, and the residue is dissolved in methanol and treated with ether. The separated (RS)-N-[[(S)-1-amidino-3-piperidinyl]methyl]-m-amino-α-2-naphthylsulfonamido-hydrocinnamamide hydrochloride is filtered off under suction and rinsed with ether; yield 0.12 g, FAB-MS: 509 $(M+H)^+$.

EXAMPLE 35 a) A solution of 50g of N-(2-naphthylsulfonyl)-3-(p-nitrophenyl)-D-alanine (Example 9b) in 100 ml of DMF is treated with 45 ml of Raney-nickel and hydrogenated at room temperature and normal pressure. The reaction solution is filtered, then concentrated and poured into water. Separated 3 -(p-aminophenyl)-N-(2-naphthylsulfonyl)-D-alanine is filtered off under suction, washed with water and dried. Yield 37.6 g, m.p. 211°–212°. MS: 370 $(M)^+$.

b) A suspension of 1.0 g of the product from a) in 15 ml of methylene chloride is treated with 1.13 ml of triethylamine. The resulting solution is cooled in an ice-bath and treated with a solution of 0.3 ml of monoethyl oxalyl chloride in 5 ml of methylene chloride. After a further 30 minutes in the ice-bath the solution is stirred at room temperature overnight. The reaction mixture is concentrated, the residue is dissolved in water and acidified with 10% citric acid and the separated product is filtered off under suction. It is dissolved in ethyl acetate, washed with water and dried. After evaporation there is obtained 0.92 of oxalic acid ester amide which, analogously to Example 5, gives 0.87 g of ethyl 4'-[(R)-2-[[[(RS)-1-amidino-3-piperidinyl] methyl]carbamoyl]-2-[(2-naphthylsulfonamido)ethyl]oxanilate hydrochloride, FAB-MS: 609 (M+H)⁺.

EXAMPLE 36

The following compounds are manufactured analogously to Example 35:

a) methyl 4'-[(R)-[[[(RS)-1-amino-3-piperidinyl]methyl] carbamoyl]-2-[(2-naphthylsulfonamido)ethyl]succinanilate hydrochloride, FAB-MS: 623 (M+H)⁺, b) methyl 3'-[(R)-2-[[[(RS)- 1-amidino-3-piperidinyl] methyl]carbamoyl]-2-(2-naphthylsulfonamido)ethyl] succinanilate hydrochloride, FAB-MS: 623 (M+H)⁺, c) benzyl 4'-[(R)-2-[[[(RS)-1-amidino-3-piperidinyl]methyl]carbamoyl]-2-[(2-naphthylsulfonamido)ethyl]succinanilate hydrochloride, FAB-MS: 699 (M+H)⁺, d) methyl 4'-[(R)-2-[[[(RS)-1-amidino-3-piperidinyl]methyl]carbamoyl]-2-[(p-iodobenzenesulfonamido)ethyl] succinanilate hydrochloride, FAB-MS: 699 (M+H)⁺, e) ethyl 4'-[(R)-2-[[[(RS)-1-amidino-3-piperidinyl]methyl]carbamoyl]-2-(2-naphthylsulfonamido]ethyl]carbanilate hydrochloride, FAB-MS: 581 (M+H)⁺.

EXAMPLE 37

Analogously to Example 35 there is obtained N-(2 -naphthylsulfonyl)-3-[p-(2-phenylglyoxylamido)phenyl]-D-alanine, MS: 502 (M⁺), which is converted analogously to Example 6e)-g) into (R)-N-[[(S)-1-amidino-3-piperidinyl] methyl]-α-(2 -naphthylsulfonyl)-p-(2-phenylglyoxylamido)hydrocinnamamide hydrochloride, FAB-MS: 641 (M+H)⁺.

EXAMPLE 38

Analogously to Examples 35 and 42, via methyl p-[p-[(R)-2-[[(RS)-1-amidino-3-piperidinyl]methyl]carbamoyl]-2-(2-naphthylsulfonamido)ethyl]benzamido]benzoate hydrochloride, FAB-MS: 671 (M+H)⁺, there is obtained p-[p-[(R)-2-[[[(RS)-1-amidino-3piperidinyl]methyl]carbamoyl]-2-(2-naphthylsulfonamido)ethyl]benzamido]benzoic acid hydrochloride, FAB-MS: 657 (M+H)⁺.

EXAMPLE 39

Analogously to Example 35 there is obtained (R)-N-[[(RS)-1 -amidino-3-piperidinyl]methyl]-p-[2-(2-methoxyethoxy)acetamido]-α-2-naphthylsulfonamidohydrocinnamamide hydrochloride, FAB-MS: 625 (M+H)⁺.

EXAMPLE 40

Analogously to Example 35 there is obtained 4'-[(R)-2-[[[(S)-1-amidino-3-piperidinyl]methyl]carbamoyl]-2-(2 -naphthylsulfonamido)ethyl]oxanilic acid hydrochloride, FAB-MS: 581 (M+H)⁺.

EXAMPLE 41

A solution of 0.7 g of 3-(p-aminophenyl)-N-(2-naphthylsulfonyl)-D-alanine (Example 35a) in 5 ml of pyridine is treated with 1 ml of acetic anhydride and left to stand at room temperature for 20 hours. After the addition of water and conc. HCl (ice-cooling) the separated product is filtered off under suction, dissolved in ethyl acetate, washed with water, dried and evaporated. The product is dissolved in 20 ml of methanolic 1N NaOH and left to stand. The solution is evaporated, the residue is dissolved in water, acidified with conc. HCl, the precipitated product is filtered off under suction, dissolved in ethyl acetate and washed with water. After evaporation the residue is reacted analogously to Example 5 and gives 146 mg of (R)-p-acetamido-N-[[(RS)-1-amidino-3-piperidinyl]methyl]-α-(2-naphthylsulfonamido)hydrocinnamamide hydrochloride, FAB-MS: 551 (M+H)⁺.

EXAMPLE 42

A suspension of 150 mg of ethyl 4'-[(R)-2-[[[(RS)-1 -amidino-3 -piperidinyl]methyl]carbamoyl]-2-(2-naphthylsulfonamido)ethyl]oxanilate hydrochloride (Example 35) in 10 ml of ethanolic 0.1N NaOH solution is dissolved at room temperature while stirring. The reaction solution is acidified with ethanolic 2.78N HCl, the separated NaCl is filtered off under suction and the filtrate is treated with ether. The separated hydrochloride is decanted off and stirred with ether. The product is filtered off under suction. Yield: 60 mg of 4'-[(R)-2-[[[(RS)-1-amidino-3-piperidinyl]methyl]carbamoyl]-2-(2-naphthylsulfonamido)ethyl]oxanilic acid hydrochloride, FAB-MS: 581 (M+H)⁺.

EXAMPLE 43

A solution of 0.5 g of benzyl 4'-[(R)-2-[[[(RS)-1-amidino-3-piperidinyl]methyl]carbamoyl]-2-(2-naphthylsulfonamido)ethyl]succinanilate hydrochloride (Example 36c) in 20 ml of ethanol is treated with 0.5 g of 10% Pd/C and hydrogenated. The catalyst is filtered off, the filtrate is concentrated and the residue is treated with ether. The separated product is decanted off, stirred with ether and finally filtered off under suction. Yield: 0.35 g of 4'-[(R)-2-[[[(RS)-1-amidino-3-piperidinyl]methyl]carbamoyl]-2-(2-naphthylsulfonamido)ethyl]succinanilidic acid hydrochloride, FAB-MS: 609 (M+H)⁺.

EXAMPLE 44

A solution of 0.5 g of 3-(p-aminophenyl)-N-(2-naphthylsulfonyl)-D-alanine (Example 35a) in 1.35 ml of 1N NaOH and 7 ml of water is treated with 6 ml of dioxane and 0.34 g of sodium hydrogen carbonate. 0.26 g of tosyl chloride is added while stirring. After stirring at room temperature for 24 hours the solution is concentrated, diluted with water and extracted with ether. The aqueous phase is treated with 6 ml of 2N HCl while cooling with ice and the separated product is filtered off under suction. The latter, without purification, is converted analogously to Example 5 into 0.39 g of (R)-N-[[(RS)-1-amidino-3-piperidinyl]methyl]-α-2-naphthylsulfonamido-p-(p-toluenesulphonamido)hydrocinnamamide hydrochloride, FAB-MS: 663 (M+H)⁺.

EXAMPLE 45

Analogously to Example 44 there is obtained (R)-N-[[(S)-1 -amidino-3-piperidinyl]methyl]-p-(p-iodobenzenesulfonamido)-α-(2-naphthylsulfonamido)hydrocinnamamide hydrochloride, FAB-MS: 775 (M+H)⁺.

EXAMPLE 46

Analogously to Example 44 via methyl p-[[p-[(R)-2-[[[(RS)-1 -amidino-3-piperidinyl]methyl]carbamoyl]-2-(2-naphthylsulfonamido)ethyl]phenyl]sulphamoyl]benzoate hydrochloride, FAB-MS: 707 (M+H)⁺, there is obtained p-[[p-[(R)-2-[[[(RS)-1 -amidino-3-piperidinyl]methyl]carbamoyl]-2-(2-naphthylsulfonamido)ethyl]phenyl]sulphamoyl]benzoic acid hydrochloride, FAB-MS: 693 (M+H)+.

EXAMPLE 47

0.45 ml of a 50% solution of ethyl glyoxylate in toluene is added to a suspension of 0.37 g of 3-(p-aminophenyl)-N-(2 -naphthylsulfonyl)-D-alanine (Example 35a) in 20 ml of dioxane. The resulting solution is treated with 0.3 g of 10% Pd/C and hydrogenated at room temperature and normal pressure for 6 hours. The catalyst is filtered off, the filtrate is evaporated and the residue is reacted as in Example 5. Yield: 89 mg of N-[p-[(R)- 2-[[[(RS)-1-amidino-3-piperidinyl]methyl]carbamoyl]-2-(2-naphthylsulfonamido)ethyl]phenyl]glycine ethyl ester hydrochloride, FAB-MS: 595 (M+H)+.

EXAMPLE 48

Analogously to Example 26 there is obtained (R)-N-[[(RS)-1 -amidino-3-piperidinyl]methyl]-1,2,3,4-tetrahydro-2-(2 -naphthylsulfonyl)-3-isoquinolinecarboxamide hydrochloride (epimers 1:1), $[\alpha]_{589}^{25}$=+76.8° (MeOH, c=0.5%), FAB-MS: 506 (M+H)+.

EXAMPLE 49

Analogously to Example 5 there is obtained (RS)-N-[[(RS)-1 -amidino-3-piperidinyl]methyl]-3-(o-aminobenzoyl)-2-(2-naphthylsulfonamido)propionamide hemisulphite, FAB-MS: 537 (M+H)+.

EXAMPLE 50

The following compounds are manufactured analogously to Example 23:

a) (S)-N-[[(RS)-1-Amidino-3-piperidinyl]methyl]-β-2 -naphthylsulfonamido-γ-oxo-4-morpholinebutyramide trifluoroacetate, FAB-MS: 531 (M+H)+.

b) (R)-N-[[(RS)-1-Amidino-3-piperidinyl]methyl] hexahydro-β-2-naphthylsulfonamido-γ-oxo-1H-azepinebutyramide trifluoroacetate, FAB-MS: 543 (M+H)+ c) (S)-N-[[(RS)-1-amidino-3-piperidinyl]methyl]hexahydro-β-2-naphthylsulfonamido-γ-oxo-1(2H)-azocinebutyramide hydrochloride, FAB-MS: 557 (M+H)+.

EXAMPLE 51 a) 5 g of potassium diphenylsulphone-3-sulphonate in 50 ml of thionyl chloride are boiled under reflux overnight. The precipitated material is filtered and, after drying, there are obtained 3.2 g of diphenylsulfone-3-sulfonyl chloride.

b) 6.7 ml of 1N sodium hydroxide solution and 2.82 g of sodium bicarbonate are added to a solution of 1.52 g of p-nitro-D-phenylalanine in 37 ml of dioxane. A solution of the product from a) in 119 ml of dioxan is added thereto and the mixture is stirred at room temperature overnight. Subsequently, the reaction mixture is poured on to ice and extracted with ethyl acetate. The organic phase is washed with water, dried and concentrated. There are thus obtained 1.75 g of 3-(p-nitro-phenyl)-N-[[(m-phenylsulfonyl)phenyl]sulfonyl]-D-alanine.

c) From the above acid there is obtained analogously to Example 6e)-g) (R)-N-[[(S)-1-amidino-3-piperidinyl]methyl]-p-nitro-≠-[m-(phenylsulfonyl)benzenesulfonamido] hydrocinnamamide hemisulfite, FAB-MS: 629 (M+H)+.

EXAMPLE 52 a) 2.3 g of p-nitro-D-phenylalanine are suspended in 25 ml of dioxan and treated with 10 ml of 1N sodium hydroxide solution and 1.7 g of sodium bicarbonate. A solution of 2.6 g of methyl 2-chlorosulfonylbenzoate in 22 ml of dioxanl is added dropwise thereto and the mixture is stirred at room temperature for 9 hours. The reaction mixture is poured into ice-cold 2N hydrochloric acid and extracted with ethyl acetate. The organic phase is washed with water, dried and evaporated. There are obtained 3.2 g of N-[[o-(methoxycarbonyl)phenyl]sulfonyl]-3-(p-nitrophenyl)-D-alanine.

b) The material obtained from a) is dissolved in 30 ml of DMF, treated with 5.3 ml of hexamethyleneimine and stirred at 80° C. for 5 hours. The reaction mixture is evaporated, the residue is taken up in ethyl acetate and shaken once against 2N hydrochloric acid and twice against water. After drying the organic phase, evaporation and chromatography of the residue on silica gel there is obtained 0.9 g of N-[[o-[(hexahydro-1H-azepin-1-yl)carbonyl]phenyl]sulfonyl]-3-(p-nitrophenyl)-D-alanine.

c) Analogously to Example 5, from the material obtained under b) there is obtained (R)-N-[[(RS)-1-amidino-3-piperidinyl]methyl]-α-[o-[(hexahydro-1H-azepin-1-yl)carbonyl]benzenesulfonamido]-p-nitrohydrocinnamamide hydrochloride, FAB-MS: 614 (M+H)+.

EXAMPLE 53

The following compounds are manufactured analogously to Example 52:

a) (R)-N-[[(RS)-1-Amidino-3-piperidinyl]methyl]-α-(p-t-butylbenzenesulfonamido)-p-nitrohydrocinnamamide acetate, FAB-MS: 545 (M+H)+.

b) (R)-N-[[(RS)-1-Amidino-3-piperidinyl]methyl]-p-nitro-α-(benzo[b]thiophensulfonamido)hydrocinnamide hydrochloride, FAB-MS: 545 (M+H)+.

EXAMPLE 54

Analogously to Examples 90a) and 23 there is obtained (13S,2RS)-N-[[(RS)-1-amidino-3-piperidinyl]methyl]-2-benzyloxymethyl-β-2-naphthylsulfonamido-γ-oxo-4-morpholinebutyramide acetate, FAB-MS: 651 (M+H)+.

EXAMPLE 55

A solution of the product from Example 54 in ethanol/1N hydrochloric acid is hydrogenated in the presence of 10% Pd/C for 30 hours under normal conditions. There is obtained (βS,2RS)-N-[[(RS)-1-amidino-3-piperidinyl]methyl]-2-hydroxymethyl-β-2 -naphthylsulfonamido-γ-oxo-4-morpholinebutyramide hydrochloride, FAB-MS: 561 (M+H)+.

EXAMPLE 56

A)a) A solution of 23.3 g of rac-2-(aminomethyl)-4-benzylmorpholine in 250 ml of dioxan is treated with 27.1 g of di-t-buty dicarbonate in 250 ml of dioxan and stirred at room temperature for 17 hours. Then, the solvent is evaporated and the residue is chromatographed on silica gel with methylene chloride/ethyl acetate (3:1). The product is recrystallized from methylene chloride/hexane and there are obtained 25.6 g of t-butyl rac-[(4-benzyl-2-morpholinyl)methylcarbamate.

A)b) A solution of the product from a) in 500 ml of ethyl acetate and 50 ml of acetic acid is treated with 2.6 g of Pd/C and hydrogenated for 5 hours at room temperature under normal conditions. After filtration and evaporation the residue is dissolved in 230 ml of DMF, treated with 46 ml of triethylamine and 10.8 g of formamidinesulphonic acid and stirred at room temperature for 20 hours. Subsequently, the reaction mixture is evaporated and the residue is partitioned between ethyl acetate and water. After drying the organic phase and evaporation there is obtained t-butyl rac-[(4-amidino-2-morpholinyl)methyl]carbamate hemisulphite.

A)c) 6.5 g of the material obtained under b) are suspended in 50 ml of methylene chloride and treated at 0° with 20 ml of TFA. After 7 hours at 0° the reaction mixture is evaporated and the residue is azeotroped with ethylene chloride and toluene. rac-2 -(Aminomethyl)-4-morpholinecarboxamidine trifluoroacetate is isolated.

B) A solution of 0.8 g of (S)-β-2-naphthylsulfonamido-γ-oxo-4-morpholinebutyric acid, obtained analogously to Example 23a)-c), in 16 ml of DMF is treated with 0.76 ml of 4-ethyl-morpholine, 0.89 g of benzotriazol-1-yloxy-tris-(dimethylamino)phosphonium hexafluorophosphate and 1.16 g of the material obtained under A)c) and the mixture is stirred at room temperature for 17 hours. Subsequently, the reaction mixture is treated with 1N hydrochloric acid and evaporated. After chromatography on a RP-18 column with water/acetonitrile there is obtained 0.5 g of (S)-N-[[(RS)-4-amidino-2-morpholinyl]methyl]-β-2-naphthylsulfonamido-γ-oxo-morpholinebutyramide hydrochloride, FAB-MS: 533 $(M+H)^+$.

EXAMPLE 57

Analogously to Example 56 there are obtained:
a) (S)-N-4-[[(RS)-4-Amidino-2-morpholinyl]methyl]-β-2-naphthylsulfonamidohexahydro-γ-oxo-1H-azepine-1-butyramide hydrochloride, FAB-MS: 545 $(M+H)^+$.
b) (S)-N-4-[[(RS)-4-Amidino-2-morpholinyl]methyl]hexahydro-β-2-naphthylsulfonamido-γ-oxo-1(2H)-azocine-1-butyramide hydrochloride, FAB-MS: 559 $(M+H)^+$.

EXAMPLE 58

Analogously to Example 8 there is obtained (R)-N-[[(RS)-1 -amidino-3-piperidinyl]methyl]-α-(2-naphthylsulfonamido)-2-oxo-3-benzoxazolinepropionamide triacetate, FAB-MS: 551 $(M+H)^+$.

EXAMPLE 59

The following compounds are manufactured analogously to Examples 8 and 56:
a) (R)-N-[[(RS)-4-Amidino-2-morpholinyl]methyl]-α-2-naphthylsulfonamido-2,3-dioxo-1-indolinepropionamide hydrochloride, FAB-MS: 565 $(M+H)^+$.
b) (R)-N-[[(RS)-4-Amidino-2-morpholinyl]methyl]-α-2-naphthylsulfonamido-2-oxo-3-benzoxazolinepropionamide hydrochloride, FAB-MS: 553 $(M+H)^+$.

EXAMPLE 60

A)a) 3.7 g of tetrabutylammonium hydrogen sulphate and 100 ml of 1N sodium hydroxide solution are added to a solution of 10.0 g of t-butyl (S)-3-aminomethyl-1-piperidinecarboxylate (Example 6d) in 400 ml of hexane and 100 ml of water. 9.3 ml of benzyl chloroformate are added dropwise to this mixture and the mixture obtained is stirred at room temperature for 3 hours. Subsequently, the organic phase is separated, washed with water, 10% citric acid, water and saturated sodium bicarbonate solution, dried and evaporated. t-Butyl (S)-3-[(1-(benzyloxy)formamido]-methyl]-1-piperidinecarboxylate is obtained.

A)b) 11.3 g of the material obtained under a) are dissolved in 120 ml of ethyl acetate, treated at 40 with 120 ml of a 4 molar solution of hydrochloric acid in ethyl acetate and stirred at room temperature for 5 hours. Subsequently, the reaction solution is concentrated, the residue is dissolved in 265 ml of DMF, treated with 18 ml of triethylamine and 4.3 g of formamidinesulphonic acid and stirred at room temperature for 17 hours. The solvent is evaporated, the residue is treated with 1N hydrochloric acid, again concentrated and chromatographed on a RP-18 column with water/acetonitrile. There are thus isolated 5.4 g of benzyl [[(S)- 1-amidino-3-piperidinyl]methyl]carbamate hydrochloride.

A)c) 6.6 g of the material obtained under b) are dissolved in 165 ml of ethanol and 165ml of 1N hydrochloric acid, treated with 1 g of Pd/C and hydrogenated under normal conditions for 2 hours. After filtration, evaporation and azeotroping with ethanol there are obtained 4.5 g of (S)-1-amidino-3-(aminomethyl)piperidine dihydrochloride, m.p. 252°–254° C., FAB-MS: 156 $(M^+)$, $[\alpha]_D$ −16.9° (c=1.0, water).

B) A solution of 1.9 g of N-(2-naphthylsulphonyl)-3-(2,3-dioxo-1-indolinyl)-D-alanine in 30 ml of DMF is treated with 2.3 ml of 4-ethylmorpholine, 2.0 g of benzotriazol-1-yloxytris(dimethylamino)phosphonium hexafluorophosphate and 1.0 g of the material obtained under A)c) and stirred at room temperature for 20 hours. The reaction mixture is concentrated, treated with 1N hydrochloric acid, again evaporated and the residue is chromatographed on silica gel with ethyl acetate/acetone/acetic acid/water (16:2:1:1): There is isolated 0.8 g of (R)-N-[(S)-1-amidino-3-piperidinylmethyl]-α-(2-naphthylsulfonamido)- 2,3-dioxo-1-indolinepropionamide acetate, FAB-MS: 563 $(M+H)^+$.

EXAMPLE 61

The following compounds are obtained analogously to Examples 8 and 60:
a) (R)-N-[[(S)-1-Amidino-3-piperidinyl]methyl]-α-2-naphthylsulfonamido-2-oxo-3-benzoxazolidinepropionamide hydrochloride, FAB-MS: 551 $(M+H)^+$,
b) (R)-N-[[(S)-1-amidino-3-piperidinyl]methyl]-5-bromo-α-2 -naphthylsulfonamido-2,3-dioxo-1-indolinepropionamide tetraacetate, FAB-MS: 643 $(M+H)^+$,
c) (R)-N-[[(S)-1-amidino-3-piperidinyl]methyl]-5-methyl-α-2 -naphthylsulfonamido-2,3-dioxo-1-indolinepropionamide acetate, FAB-MS: 577 $(M+H)^+$,
d) (R)-N-[[(S)-1-amidino-3-piperidinyl]methyl]-α-[(p-iodophenyl)sulfonyl]-2,3-dioxo-1-indolinepropionamide hydrochloride, FAB-MS: 639 $(M+H)^+$,
e) (R)-N-[[(S)-1-amidino-3-piperidinyl]methyl]-α-(o-nitrobenzenesulfonamido)- 2,3-dioxo-1-indolinepropionamide hydrochloride, FAB-MS: 558 $(M+H)^+$.

EXAMPLE 62 a) A solution of 21.4 g of 2-naphthylsulfonyl chloride in 200 ml of ether is added dropwise while stirring to a solution of 15 g of N-α-Z-L-2,3-diaminopropionic acid in 189ml of 1N sodium hydroxide solution. The mixture is left to stir for a further 6 hours. Subsequently, the reaction mixture is poured into ice-cold 2N hydrochloric acid and extracted with ethyl acetate. The organic is washed with water, dried and evaporated. After chromatography of the residue on silica gel with methylene chloride/methanol/acetic acid (94:5:1) there are isolated 17.9 g of N-[(benzyloxy)carbonyl]-3-(2-naphthylsulfonamido)-L-alanine.

b) From the material obtained under a) there is manufactured analogously to Example 5 benzyl [(S)-1-[[[(RS)-1-amidino-3-piperidinyl]methyl]carbamoyl-2-(2-naphthylsulfonamido)ethylcarbamate, FAB-MS: 567 (M+H)$^+$.

EXAMPLE 63 a) A solution of 1.1 g of the product from Example 62b) in 22 ml of 1N hydrochloric acid and 11 ml of ethanol is treated with 0.2 g of Pd/C and hydrogenated under normal conditions for 5 hours. After filtration and evaporation, there is obtained 0.96 g of (S)-[[(RS)-1-amidino-3-piperidinyl]methyl]-2-amino-3-(2naphthylsulfonamido)propionamide dihydrochloride, FAB-MS: 433 (M+H)$^+$.

b) A solution of 0.95 g of the material obtained under a) in 20 ml of DMF is treated with 0.24 ml of 4-ethylmorpholine and 0.3 g of phthalic anhydride and stirred at 50° for 6 hours. The reaction mixture is evaporated and the residue is chromatographed over a RP-18 column with water/acetonitrile. There is obtained 0.3 g of o-[[(S)-1-[[[(RS)-1-amidino-3-piperidinyl]methyl]carbamoyl]-2-(2-naphthylsulfonamido)ethyl]carbamoyl]benzoic acid, FAB-MS: 581 (M+H)$^+$.

EXAMPLE 64

A solution of 1.4 g of the product from Example 63a) in 28 ml of DMF is treated with 1.05 ml of 4-ethylmorpholine, 1.23 g of benzotriazol-1-yloxy-tris(dimethylamino)phosphonium hexafluorophosphate and 0.95 g of o-(benzyloxy)benzoic acid and stirred at room temperature overnight. The reaction mixture is evaporated and the residue is partitioned between ethyl acetate and water. The organic phases are dried and evaporated, and the residue is chromatographed on silica gel with ethyl acetate/acetone/acetic acid/water (16:2:1:1). There is isolated 0.2 g of (S)-2-N-[o-(benzyloxy)benzamido]-3-(2-naphthylsulfonamido)-N-[[(RS)-1-amidino-3-piperidinyl]methyl]propionamide acetate, FAB-MS: 643 (M+H)$^+$.

EXAMPLE 65 a) t-Butyl (R)-2-[[(S)-1-[[[(RS)-1-amidino-3-piperidyl]methyl]carbamoyl]-2-(2-naphthylsulfonamido)ethyl]carbamoyl]-1-piperidinecarboxylate trifluoroacetate, FAB-MS: 644 (M+H)$^+$, is obtained analogously to Example 64 using t-butyl-(R)-2-piperidinecarboxylic acid in place of o-(benzyloxy)benzoic acid.

b) A solution of 300 mg of the product from a) in 5 ml of ethyl acetate is treated with 5 ml of a 4 molar hydrochloric solution in ethyl acetate. After stirring at room temperature for 3 hours the suspension is evaporated and there is isolated (R)-N-(S)- 1-[[[(RS)-1-amidino-3-piperidinyl]methyl]carbamoyl]-2-(2-naphthylsulfonamido)-2 -piperidinecarboxamide dihydrochloride, FAB-MS: 544 (M+H)$^+$.

EXAMPLE 66

A solution of 120 mg of the product from Example 64 in 12 ml of acetic acid is treated with 50 mg of Pd/C and hydrogenated under normal conditions for 6 hours. After filtration and evaporation there are obtained 80 mg of (S)-N-[[(RS)-1-amidino-3-piperidinyl]methyl]-2-(2-hydroxybenzamido)-3-(2-naphthylsulfonamido)propionamide acetate, FAB-MS: 553 (M+H)$^+$.

EXAMPLE 67 a) The material obtained according to Example 62a) is reacted analogously to Example 6a)-e). There is obtained t-butyl (S)-3-[[[N-[(benzyloxy)carbonyl]-3-(2-naphthylsulphonamido)-L-alanyl]amino]methyl]-1-piperidinecarboxylate, FAB-MS: 525 (M+H)$^+$Boc.

b) A solution of 3.0 g of the material obtained according to a) in 80 ml of ethyl acetate/acetic acid (1:1) is treated with 0.8 g of Pd/C and hydrogenated under normal conditions for 48 hours. After filtration and evaporation the residue is dissolved in 25 ml of DMF, 1.6 ml of 4-ethylmorpholine and 0.81 g of isatoic anhydride are added thereto and the mixture is stirred at 80° for 16 hours. The solvent is evaporated and the residue is partitioned between ethyl acetate and water. The organic phase is washed with water, dried and evaporated, and the residue is chromatographed on silica gel with methylene chloride/ethyl acetate (3:1). There are isolated 1.3 g of t-butyl (S)-3-[[[N-anthraniloyl- 3-(2-naphthylsulfonyl)-L-alanyl]amino]methyl]-1 -piperidinecarboxylate FAB-MS: 610 (M+H)$^+$.

c) From the material isolated according to b) there is obtained analogously to Example 6f-g) N-[(S)-1-[[[(S)-1-amidino-3-piperidinyl]methyl]carbamoyl]-2-( 2-naphthylsulfonamido)ethyl]-o-aminobenzamide hemisulfite, FAB-MS: 552 (M+H)$^+$.

EXAMPLE 68

Analogously to Example 23a)-c) and Example 60B) using ethyl rac-trans-4-methyl-2-piperidinecarboxylate in place of benzylamine there is obtained ethyl (2RS,4R)-1-[(S)-3-[[[(S)-1 -amidino-3-piperidinyl]methyl]carbamoyl]-2-(2-naphthylsulfonamido)propionyl]-4-methyl-2-piperidinecarboxylate acetate (epimers 1:1), FAB-MS: 615 (M+H)$^+$.

EXAMPLE 69

By treating the product from Example 68 with methanolic sodium hydroxide solution there is obtained (2RS,4R)-1-[N$^4$-[[(S)- 1-amidino-3-piperidinyl]methyl]-N$^2$-(2-naphthylsulfonyl)-L-asparaginyl]-4-methyl-2-piperidinecarboxylic acid (epimers 1:1), FAB-MS: 587 (M+H)$^+$.

EXAMPLE 70 a) 22.4 ml of 2N NaOH are added dropwise at 10° C. to a solution of 5 g of D-aspartic acid β-benzyl ester and 5.07 g of 2-naphthylsulphonyl chloride in 80 ml of dioxan cooled to 10° C. The reaction mixture is subsequently stirred at room temperature for 2 hours and then treated with 25 ml of 1N hydrochloric acid. After evaporation of the dioxan the residue is taken up in ethyl acetate and washed with water. After drying and evaporation of the ethyl acetate phase there are obtained 9.1 g of 4-benzyl 1-hydrogen N-(2-naphthylsulfonyl)-D-aspartate, Rf=0.53 (ethyl acetate/glacial acetic acid 0.97:0.03).

b) 3.72 ml of Hünig base, 9.67 g of benzotriazol-1-yloxy-tris(dimethylamino)phosphonium hexafluorophosphate and 4.68 g of t-butyl (S)-3-aminomethyl-1-piperidinecarboxylate are added in succession while stirring to the product from a) in 100 ml of DMF. The reaction mixture is stirred for 4 hours, subsequently taken up in ether and the ether phase is washed with water. After drying and evaporation of the ether phase the residue is chromatographed over silica gel with ether/hexane (9:1). There are obtained 9.1 g of benzyl (R)-3-[[[(S)-1-(t-butoxycarbonyl)- 3-piperidinyl]methyl]carbamoyl]-3-(2 -naphthylsulfonamido)-propionate, Rf=0.35 (ether/hexane 9:1).

c) 3.0 g of the product from b) are dissolved in 60 ml of methanol and, after the addition of 10% Pd/C, hydrogenated at room temperature under normal pressure. After 8 hours the catalyst is filtered off and the methanol solution is concentrated. There are obtained 2.38 g of (R)-3-[[[(S)-1-(t-butoxycarbonyl)-3 -piperidinyl]methyl]carbamoyl]-3-(2-naphthylsulfonamido)propionic acid, Rf=0.08 (ethyl acetate).

d) 1 g of carboxylic acid from c) in 18 ml of methylene chloride is cooled to −23° C. and there are added thereto in succession 0.25 ml of N-methylmorpholine and 0.3 ml of isobutyl chloroformate. Then, the reaction mixture is stirred at −23° and treated with 0.36 ml of ethyl piperidine-3-carboxylate. The reaction mixture is subsequently taken up in 100 ml of ether. The ether solution is washed with 1N hydrochloric acid and with water. After drying and evaporation of the ether phase the residue is chromatographed over silica gel with ethyl acetate/hexane (4:1). There are obtained 917 mg of ethyl (R,S)-1-[(R)-3 -[[[(S)-1-(t-butoxycarbonyl)-3-piperidinyl]methyl]carbamoyl]-3 -(2-naphthylsulfonamido)propionyl]-3-piperidinecarboxylate, Rf=0.4 (ethyl acetate/hexane 4:1).

e) 1.2 ml of trifluoroacetic acid are added while stirring to a solution of 400 mg of the product from d) in 9.5 ml of methylene chloride. The methylene chloride and the trifluoroacetic acid are subsequently evaporated at 50° C. The residue is dissolved in methanol and the methanol solution is treated with 0.42 ml of triethylamine and 150 mg of formamidinesulphonic acid. The reaction mixture is subsequently stirred at room temperature for 8 hours. A further 0.09 ml of triethylamine and 75 mg of formamidinesulphonic acid are added three times at intervals of 2 hours. The reaction mixture is concentrated, the residue is suspended in 20 ml of Takeda solution/ethyl acetate (1:1) (Takeda solution=ethyl acetate/acetone/water/glacial acetic acid 6:2:1:1) and filtered. The filtrate is concentrated and the residue is subsequently chromatographed over silica gel with Takeda solution/ethyl acetate (1:1). From the chromatography there are obtained 114 mg of ethyl (RS)-1-[(R)-[[(S)-1-amidino-3-piperidinyl]methyl]carbamoyl]-3-(2-naphthylsulfonamido)propionyl]-3-piperidinecarboxylate acetate, Rf=0.34 MS (EI): 601 (M+H).

EXAMPLE 71

The following compounds are manufactured analogously to Example 70:

a) [(R)-1-[(S)-3-[[(S)-1-Amidino-3-piperidinyl]methyl]carbamoyl]-3-(2-naphthylsulfonamido)propionyl]-3 -piperidinyl]methyl acetate, Rf=0.61 (Takeda solution), FAB-MS: 601 (M+1).

b) [(S)-1-[(S)-3-[[(S)-1-Amidino-3-piperidinyl]methyl] carbamoyl]-3-(2-naphthylsulfonamido)propionyl]-3-piperidinyl]methyl p-tosylate (1:1), Rf=0.29 (Takeda solution), FAB-MS: 601 (M+1).

c) Methyl (RS)-1-[(R)-3-[[[(S)-1-amidino-3-piperidinyl] methyl]carbamoyl]-3-(2-naphthylsulfonamido)propionyl]-4-oxo- 3-piperidinecarboxylate acetate (1:1), Rf=0.27 (Takeda solution), FAB-MS: 601 (M+1).

d) [(S)-1-[(R)-3-[[(S)-1-Amidino-3-piperidinyl]methyl] carbamoyl]-(2-naphthylsulfonamido)acetyl]-3-piperidinyl]methyl acetate acetate, Rf=0.29 (Takeda solution), FAB-MS: 601 (M+1).

e) [(R)-1-[(R)-3-[[(S)-1-Amidino-3-piperidinyl]methyl] carbamoyl]-(2-naphthylsulphonamido)acetyl]-3-piperidinyl]methyl acetate acetate, Rf=0.35 (Takeda solution), FAB-MS: 601 (M+1).

f) Diethyl (RS)-1-[(R)-[[(S)-1-amidino-3-piperidinyl]methyl]carbamoyl]-3-(2-naphthylsulfonamido)propionyl] -3-piperidinecarboxamide acetate, Rf=0.3 (Takeda solution), FAB-MS: 628 (M+1).

g) [(S)-1-[(S)-3-[[[(S)-1-Amidino-3-piperidinyl]methyl] carbamoyl]-3-(2-naphthylsulfonamido)propionyl]-3piperidinyl]methyl isobutyrate acetate, Rf=0.43 (Takeda solution), MS (EI): 629 (M+1).

h) [(S)-1-[(S)-3-[[[(S)-1-Amidino-3-piperidinyl]methyl] carbamoyl]-3-(2-naphthylsulfonamido)propionyl]-3-piperidinyl]methyl butyrate acetate, Rf=0.47 (Takeda solution), FAB-MS: 629 (M+1).

i) Ethyl (3R,4R)-4-acetoxy-1-[(R)-3-[[[(S)-1-amidino-3piperidinyl]methyl]carbamoyl]-3-(2-naphthylsulphonamido)propionyl]-3-piperidine carboxylate acetate (1:1), Rf=0.21 (Takeda solution), FAB-MS: 659 (M+1).

j) Ethyl (3S,4S)-4-acetoxy-1-[(R)-3-[[[(S)-1-amidino-3 -piperidinyl]methyl]carbamoyl]-3-(2-naphthylsulphonamido)propionyl]-3-piperidincarboxylate acetate (1:1), Rf=0.24 (Takeda solution), FAB-MS: 659 (M+1).

S-Aspartic acid 13-benzyl ester is used in place of D-aspartic acid β-benzyl ester (Example 70a)) for the manufacture of the products a), b), g) and h).

The intermediates for the manufacture of the products a), b), d), e), i) and j) are synthesized according to the following method: 2.0 g of t-butyl (S)-3-hydroxymethyl-1-piperidinecarboxylate or t-butyl (R)-3-hydroxymethyl-1-piperidinecarboxylate are stirred for 30 minutes together with 0.88 ml of acetic anhydride, 26.3 mg of dimethylaminopyridine and 3.0 ml of pyridine. The reaction mixture is subsequently taken up in ether and the ether phase is washed with 20% citric acid, saturated sodium bicarbonate solution and water. After drying and evaporation of the ether phase the 2.44 g of product, Rf=0.85 (ether), are dissolved in 50 ml of methylene chloride and treated with 12 ml of trifluoroacetic acid. The reaction solution is stirred for 30 minutes and subsequently concentrated to dryness. The (S)- or (R)-3-acetoxymethyl-1-piperidinecarboxylic acid trifluoroacetic acid salt, Rf=0.14 (Takeda solution), is used in d) with an equivalent amount of triethylamine.

The intermediates for the synthesis of the products of Examples g) and h) are prepared as follows:

170 mg of dimethylaminopyridine and 3.4 mg of pyridine are added to 3.0 g of t-butyl (S)-3-hydroxymethyl-1-piperidinecarboxylate. 1.66 ml of isobutyryl chloride are added dropwise thereto. The reaction mixture is then concentrated. The residue is taken up in ether and the ether phase is washed in succession with 20 ml of citric acid, water, sodium bicarbonate solution and water. After drying and evaporation of the ether phase there are obtained 3.9 g of t-butyl (S)-3-isobutyroxymethyl-1-piperidinecarboxylate, Rf=0.87 (ether). 3.09 g of this ester are dissolved in 80 ml of methylene chloride and treated with 20 ml of trifluoroacetic acid. After stirring for 30 minutes the solution is concentrated. 30 ml of methanol are added to the residue and saturated sodium bicarbonate solution is then added dropwise. The aqueous phase is extracted with methylene chloride and the methylene chloride extracts are dried and concentrated. There are obtained 2.82 g of (S)-3-iso- butyroxymethyl-1-piperidinecarboxylic acid trifluoroacetic acid salt, Rf=0.4 (Takeda solution).

(S)-3-Butyroxymethyl-1-piperidinecarboxylic acid trifluoroacetic acid salt, Rf=0.4 (Takeda solution) is obtained according to the same method.

EXAMPLE 72 a) 14.4 ml of triethylamine are added dropwise to 6.91 g of glycine t-butyl ester hydrochloride and 12.1 g of 2-naphthylsulfonyl chloride in 70 ml of methylene chloride. The reaction mixture is subsequently diluted with 200 ml of ether. The organic phase is washed with 1N hydrochloric acid and with water. After drying and evaporation the residue is suspended in ether and suction filtered. After drying the crystals there are obtained 11.57 g of N-(2-naphthylsulfonyl)-glycine t-butyl ester, Rf=0.49 (ether/hexane 2:1).

b) 1 g of the product from a), 923 mg of dansyl chloride, 0.48 mg of triethylamine and 418 mg of dimethylaminopyridine are stirred together in 10 ml of methylene chloride. The reaction mixture is taken up in 100 ml of ether and washed with 1N hydrochloric acid and with water. After drying and evaporation there are obtained 1.67 g of N-[[5-(dimethylamino)-1-naphthyl]sulfonyl]-N-(2-naphthylsulfonyl)glycine, Rf=0.33 (methylene chloride/n-hexane 9:1).

c) Hydrochloric acid gas is conducted at 0° to 5° C. through a solution of the product from b) in 17 ml of methylene chloride. After concentration of the reaction solution there are obtained 1.7 g of carboxylic acid, Rf=0.72 (ethyl acetate/glacial acetic acid 97:3). 844 mg of dicyclohexylcarbodiimide (DCC) are added to a solution of this product in 17 ml of methylene chloride at room temperature. Then, 877 mg of t-butyl (S)-3-aminomethyl-1-piperidinecarboxylate dissolved in 3 ml of methylene chloride are added thereto. The reaction mixture is filtered, the filtrate is evaporated and the residue is chromatographed over silica gel with methylene chloride/ether (9:1). There is obtained 0.82 g of t-butyl (S)-3-[[N-[[5-(dimethylamino-1-naphthyl]sulfonyl]-N-(2-naphthylsulfonyl)glycyl]amino]methyl]-1-piperidinecarboxylate, Rf=0.2 (methylene chloride/ether 9:1). This 0.82 g is converted analogously to Example 70e) into 316 mg of N-[[(S)-1-amidino-3-piperidinyl]methyl]-2-[[[5-(dimethylamino)-1-naphthyl]sulfonyl](2-naphthylsulfonyl)amino]acetamide acetate, Rf=0.46 (Takeda solution). FAB-MS: 637 (M+1).

EXAMPLE 73

Analogously to Example 30, but using 2-thienylglyoxalic acid, benzoic acid and, respectively, benzylchloroformate in place of phenylglyoxalic acid (Example 30g) there are obtained:

a) (R)-N-[[(S)-1-Amidino-3-piperidinyl]methyl]-2-(2-naphthylsulfonamido)-3-(α-oxo-2-thiophenacetamido)propionamide p-toluenesulfonate (1:1), FAB-MS: 571 (M+H)+, b) N-[(R)-2-[[[(S)-1-amidino-3-piperidinyl]methyl]carbamoyl]-2-(2-naphthylsulfonamido)ethyl]benzamide p-toluenesulfonate (1:1), FAB-MS: 537 (M+H)+, bzw.

c) benzyl-[(R)-2-[[[(S)-1-amidino-3-piperidinyl]methyl]carbamoyl]-2-(2-naphthylsulfonamido]ethyl]carbamate acetate (1:1), FAB-MS: 567 (M+H)+.

EXAMPLE 74

From the product of Example 27 by treatment with aqueous sodium hydroxide solution there is obtained o-[[(R)-α-[[[(RS)-1 -amidino-3-piperidinyl]methyl]carbamoyl]-p-nitrophenethyl]sulfamoyl]benzoic acid, FAB-MS: 533 (M+H)+.

EXAMPLE 75

Analogously to Examples 68 and 69 there is obtained (R)-4-[(S)-3-[[[(S)-1-amidino-3-piperidinyl]methyl]carbamoyl]-2-(2 -naphthylsulfonamido)propionyl]hexahydro-1,4-oxazepine-3-carboxylic acid, FAB-MS: 589 (M+H+.

EXAMPLE 76

Analogously to Example 52 (but using 2-naphthylsulfonyl chloride) and Example 60 there is obtained p-[(RS)-2-[[[(S)-1 -amidino-3-piperidinyl]methyl]carbamoyl]-2-(2 -naphthylsulfonamido)-ethyl]benzoic acid, FAB-MS: 538 (M+H)+.

EXAMPLE 77

Analogously to Example 43 there is obtained 4'-[(R)-2-[[[(S)-1-amidino-3-piperidinyl]methyl]carbamoyl]-2-(2-naphthylsulfonamido)ethyl]succinanilidic acid, FAB-MS: 609 (M+H)+.

A compound of formula I, a solvate or salt thereof can be used in a known manner as the active substance for the manufacture of pharmaceutical preparations, for example, of tablets and capsules of the following composition:

|  | Per tablet |
|---|---|
| Active substance | 200 mg |
| Microcrystalline cellulose | 155 mg |
| Maize starch | 25 mg |
| Talc | 20 mg |
| Hydroxypropylmethyl cellulose | 20 mg |
|  | 425 mg |

Example A

|  | Per capsule |
|---|---|
| Active substance | 100.0 mg |
| Maize starch | 20.0 mg |
| Lactose | 95.0 mg |
| Talc | 4.5 mg |
| Magnesium stearate | 0.5 mg |
|  | 220.0 mg |

Example B

We claim:
1. A compound of the formula

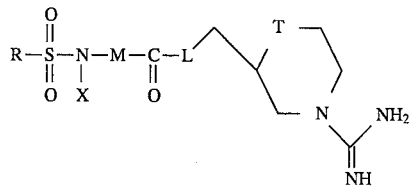

wherein

R is aryl, heteroraryl or heterocyclcyl;
L is NH or O;

X is H, —CH₂COOH, —CH₂COO—C₁₋₄-alkyl, —CH₂CO— (tetra- to heptamethyleneimino) or optionally N- mono- or N- di-C₁₋₄-alkylated —CH₂CONH₂;

M is a substituted ethylene group of the formula —CH₂[R'—(CO)₁₋₂NH]CH—, —CH₂(benzyl-OCONH)CH—OR—CH(CO—Q)CH₂—; and R' is aryl, heteroaryl, cycloalkyl or heterocyclyl;

Q is benzylamino or a tetra- to heptamethyleneimino group optionally substituted by up to 2 substituents from the group C₁₋₄-alkyl, COOH, —COO—C₁₋₄-alkyl, —CH₂OH and —CH₂O-benzyl, a hydrate or solvate, or physiologically usable salt thereof.

2. A compound according to claim 1 of the formula

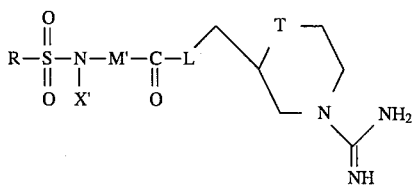

IA wherein

X' is H, —CH₂COOH, —CH₂COO—C₁₋₄-alkyl, —CH₂CO— tetra- to heptamethyleneimino or optionally N- mono- or N- di-C₁₋₄-alkylated —CH₂CONH₂, and M' is a —CH(CO—Q')CH₂— group, Q' is a benzylamino, morpholino or tetra- to heptamethyleneimino, or a hydrate or solvate or physiological usable salt thereof.

3. A compound of claim 2, wherein X' is H.

4. A compound according to claim 1 of the formula

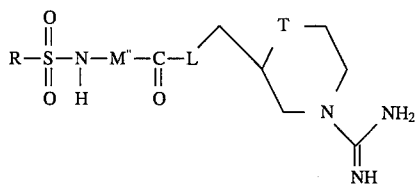

IB wherein

M" is a —CH₂[R'—(CO)₁₋₂NH]CH—, —CH₂(benzyl-OCONH)CH— or —CH(CO—Q")CH₂— group

Q" is a tretra- to heptamethyleneimino group optionally interrupted by an O or S atom and optionally substituted by up to 2 substituents selected from the group consisting of C₁₋₄-alkyl, —COOH, —COO—C₁₋₄-alkyl, —CH₂OH and —CH₂O-benzyl.

5. A compound according to claim 1 selected from the group consisting of (S)-N-[(RS)-1-amidino-3-piperidinylmethyl]hexadyro-β-(2-naphthylsulfonamido)-γ-oxo-1H-1-azepinebutyramide, (S)-N-[[(RS)-1-amidino-3-piperidinyl]methyl]hexahydro-β-2-naphthysulfonamido-γ-oxo-1(2H)-azocine butyramide, (2RS,4R)-1-[N⁴-[[(S)-1-amidino-3-piperidinyl]methyl]-N²-(2-naphthylsulfonyl)-L-asparaginyl]-4-methyl-2-piperidine carboxylic acid, (S)-N-[(RS)-1-amidino-3-piperidinylmethyl]-3-benzylcarbamoyl-3-(2-naphthylsulfonamido)proprionamide, (R)-N-[(RS)-1-amidino-3-piperidinylmethyl]-3-benzylcarbamoyl-3-(2-naphthylsulfonamido)propionamide, (S)-N-[[(RS)-1-amidino-3-piperidinyl]methyl]-β-2-naphthylsulfonamido-γ-oxo-4-morpholinebutyramide, (R)-N-[[(RS)-1-amidino-3-piperidinyl]methyl]hexahydro-β-2-naphthylsulfonamido-γ-oxo-1H-azepinebutyramide, (βS,2RS)-N-[[(RS)-1-amidino-3-piperidinyl]methyl]-2-benzyloxymethyl-β-2-naphthylsulfonamido-γ-oxo-4-morpholinebutyramide, (βS,2RS)-N-[[(RS)-1-amidino-3-piperidinyl]methyl]-2-hydroxymethyl-β-2-(naphthylsulfonamido-γ-oxo-4 morpholine butyramide,

[(S)-1-[[[(RS)-1-amidino-3-piperidinyl]methyl]carbamoyl- 2-(2-naphthylsulfonamido)-ethylcarbamate, O-[[(S)-1-[[[(RS)-1-amidino-3-piperidinyl]methyl]carbamoyl]-2-(2-naphthylsulfonamido)ethyl]carbamoyl] benzoic acid, (S)-2-N-[o-(benzyloxy)benzamido]-3-(2-naphthylsulfonamido)-N-[[RS]-1-amidino-3-piperidinyl]methyl] propionamide, (R)-N-(S)-1-[[[(RS)-1-amidino-3-piperidinyl]methyl] carbamoyl]-2-(2-naphthylsulfonamido)-2-piperidine carboxamide, (S)-N-[[(RS)-1-amidino-3-piperidinyl]methyl]-2-(2-hydroxybenzamido)-3-(2-naphthylsulfonamido)propionamide, N-[(S)-1-[[[(S)-1-amidino-3-piperidinyl]methyl]carbamoyl]-2-(2-naphthylsulfonamido)ethyl]-o-aminobenzamide, ethyl(2RS,4R)-1-[(S)-3-[[[(S)-1-amidino-3-piperidinyl] methyl]carbamoyl]-2-(2-naphthylsulfonamido)proprionyl]-4-methyl-2-piperidine carboxylate, and (R)-4-[(S)-3-[[[(S)-1-amidino-3-piperidinyl]methyl]carbamoyl]-2-(2-naphthysulfonamido)propionyl]hexahydro-1,4-oxazepine-3-carboxylic acid.

6. A compound according to claim 1, wherein X is other than H.

7. A compound according to claim 1, wherein R is naphthyl, hydroxynaphthyl, 4-biphenyl, 2-anthryl, iodophenyl, nitrophenyl, benzyloxyphenyl, dimethoxyphenyl, 4-methoxy-2,3,6-trimethylphenyl, 2,4,6-triisopropylphenyl, carboxyphenyl, methoxycarbonylphenyl, benzyloxynaphthyl, phenylsulfonylphenyl, hexahydroazepinoylphenyl or t-butylphenyl.

8. A compound according to claim 1, wherein R is 3-methyl-8-quinolyl, 5-(1-methyl-5-trifluoromethylpyrazol-3-yl)-2-thienyl or benzothienyl.

9. A compound according to claim 1, wherein R is 3-methyl-1,2,3,5-tetrahydro-8-quinolyl.

10. A compound according to claim 1, wherein X is H or —CH₂COOH.

11. A compound according to claim 1, wherein M is 2-(carboxybenzoylamido)ethylene, 2-(benzyloxybenzoylamido)ethylene, 2-(2-piperidinecarboxamido)ethylene, 2-(hydroxybenzoylamido)ethylene or 2-(aminobenzoylamido)ethylene.

12. A compound according to claim 1, wherein M is 1-(benzylaminocarbonyl)-ethylene, 1-(hexahydroazepinoyl) ethylene, 1-(morpholinoyl)-ethylene, 1-(heptahydroazocinoyl)ethylene, 1-[2-(benzyloxy methylmorpholinoyl)]ethylene, 1-[2-(hydroxymethylmorpholinoyl)]ethylene, 1-(2-ethoxycarbonyl-4-methylpiperidinoyl)ethylene, 1-(2-carboxy-4-methylpiperidinoyl)ethylene or 1-(3-carboxy-hexahydro-1,4-oxazepinoyl)ethylene.

13. A compound according to claim 1, wherein R is naphthyl or nitro- or iodophenyl, L is NH and the asymmetric C atom in the piperidine ring has the (S)-configuration.

14. A pharmaceutical composition comprising an effective amount of a compound of the formula

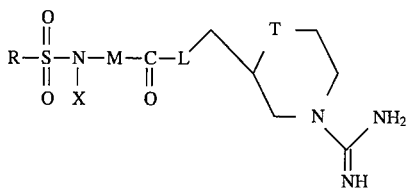

wherein
R is aryl, heteroraryl or heterocyclyl;
L is NH or O;
X is H, —CH$_2$COOH, —CH$_2$COO—C$_{1-4}$-alkyl, —CH$_2$CO— (tetra- to heptamethyleneimino) or optionally N- mono- or N-di-C$_{1-4}$-alkylated —CH$_2$CONH$_2$;
M is a substituted ethylene group of the formula: —CH$_2$[R'—(CO)$_{1-2}$NH]CH—, —CH$_2$(benzyl-OCONH)CH— or —CH(CO—Q)CH$_2$—;
R' is aryl, heteroaryl, cycloalkyl or heterocyclyl; and
Q is benzylamino or a tetra- to heptamethyleneimino group optionally substituted by up to 2 substituents from the group C$_{1-4}$-alkyl, COOH, —COO—C$_{1-4}$-alkyl, —CH$_2$OH and —CH$_2$O-benzyl, a hydrate or solvate, or physiologically usable salt thereof.

15. A pharmaceutical composition according to claim 14, wherein the compound is a compound of the formula

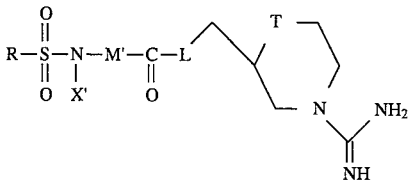

wherein
X' is H, —CH$_2$COOH, —CH$_2$COO—C$_{1-4}$-alkyl, —CH$_2$CO— tetra- to heptamethyleneimino or optionally N- mono- or N- di-C$_{1-4}$-alkylated —CH$_2$CONH$_2$ and
M' is a —CH(CO—Q')CH$_2$— group,
Q' is benzylamino, morpholino or tetra- to heptamethyleneimino,
R,R' and L have the same significances as in claim 14, as well as hyrates or solvates and physiological usable salts thereof.

16. A pharmaceutical composition according to claim 14 wherein X is H.

17. A pharmaceutical composition according to claim 14 wherein the compound is of the formula

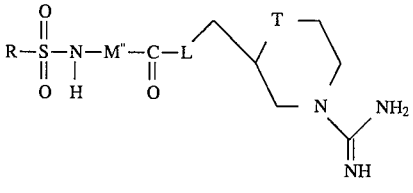

wherein
M" is a —CH$_2$[R'—(CO)$_{1-2}$NH]CH—, —CH$_2$(benzyl-OCONH)CH— or —CH(CO—Q')CH$_2$ group,
Q' is a tetra- to heptamethyleneimio group optionally interrupted by an O or S atom and optionally substituted by up to 2 substituents selected from the group consisting of C$_{1-4}$-alkyl, —CH$_2$OH and —CH$_2$O-benzyl and R,R' and L have the same significances as given in claim 14.

18. A pharmaceutical composition according to claim 14, wherein the compound is selected from the group consisting of:

(S)-N-[(RS)-1-amidino-3-piperidinyl methyl]hexadyro-β-(2-naphthylsulfonamido)-γ-oxo-1H-1-azepinebutyramide, (S)-N-[[(RS)-1-amidino-3-piperidinyl]methyl]hexahydro-β-2-naphthysulfonamido-γ-oxo-1(2H)-azocine butyramide, (2RS,4R)-1-[N$^4$-[[(S)-1-amidino-3-piperidinyl]methyl]-N$^2$-(2-naphthylsulfonyl)-L-asparaginyl]-4-methyl-2 -piperidine carboxylic acid, (S)-N-[(RS)-1-amidino-3-piperidinylmethyl]-3 -benzylcarbamoyl-3-(2-naphthylsulfonamido)proprionamide, (R)-N-[(RS)-1-amidino-3-piperidinylmethyl]-3 -benzylcarbamoyl-3-(2-naphthylsulfonamido)propionamide, (S)-N-[[(RS)-1-amidino-3-piperidinyl]methyl]-β-2 -naphthylsulfonamido-γ-oxo-4-morpholinebutyramide, (R)-N-[[(RS)-1-amidino-3-piperidinyl]methyl]hexahydro-β-2-naphthylsulfonamido-γ-oxo-1H-azepinebutyramide, (βS,2RS)-N-[[(RS)-1-amidino-3-piperidinyl]methyl]-2-benzyloxymethyl-β-2-naphthylsulfonamido-γ-oxo-4-morpholinebutyramide, (βS,2RS)-N-[[(RS)-1-amidino-3-piperidinyl]methyl]-2-hydroxymethyl-β-2-naphthylsulfonamido-γ-oxo-4 morpholine butyramide,

[(S)-1-[[[(RS)-1-amidino-3-piperidinyl]methyl]carbamoyl- 2-(2-naphthylsulfonamido)-ethylcarbamate, O-[[(S)-1-[[[(RS)-1-amidino-3-piperidinyl]methyl]carbamoyl]-2-(2-naphthylsulfonamido)ethyl]carbamoyl] benzoic acid, (S)-2-N-[o-(benzyloxy)benzamido]-3-(2 -naphthylsulfonamido)-N-[[RS)-1-amidino-3 -piperidinyl]methyl] propionamide, (R)-N-(S)-1-[[[(RS)-1-amidino-3 -piperidinyl]methyl] carbamoyl]-2-(2 -naphthylsulfonamido)-2-piperidine carboxamide, (S)-N-[[(RS)-1-amidino-3-piperidinyl]methyl]-2-(2 -hydroxybenzamido)-3-(2-naphthylsulfonamido)propionamide, N-[(S)-1-[[[(S)-1-amidino-3 -piperidinyl]methyl]carbamoyl]-2-(2 -naphthylsulfonamido)ethyl]-o-aminobenzamide, ethyl(2RS,4R)-1-[(S)-3-[[[(S)-1-amidino-3 -piperidinyl] methyl]carbamoyl]-2-(2 -naphthylsulfonamido)proprionyl]-4-methyl-2-piperidine carboxylate, and (R)-4-[(S)-3-[[[(S)-1-amidino-3 -piperidinyl]methyl]carbamoyl]-2-(2 -naphthysulfonamido)propionyl]hexahydro-1,4 -oxazepine-3-carboxylic acid.

19. A pharmaceutical composition according to claim 14, wherein X is other than hydrogen.

20. A pharmaceutical composition according to claim 14, wherein R is naphthyl, hydroxynaphthyl, 4-biphenyl, 2-anthryl, iodophenyl, nitrophenyl, benzyloxyphenyl, dimethoxyphenyl, 4 -methoxy-2,3,6-trimethylphenyl, 2,4,6-triisopropylphenyl, carboxyphenyl, methoxycarbonylphenyl, benzyloxynaphthyl, phenylsulfonylphenyl, hexahydroazepinoylphenyl or t-butylphenyl.

21. A pharmaceutical composition according to claim 14, wherein R is 3-methyl-8-quinolyl, 5-(1-methyl-5 -trifluoromethylpyrazol-3-yl)-2-thienyl or benzothienyl.

22. A pharmaceutical composition according to claim 14, wherein R is 3-methyl-1,2,3,5-tetrahydro-8-quinolyl.

23. A pharmaceutical composition according to claim 14, wherein X is H or —CH₂COOH.

24. A pharmaceutical composition according to claim 14, wherein M is a 2-(carboxybenzoylamido)ethylene, 2-(benzyloxybenzoylamido)ethylene, 2-(2-piperidinecarboxamido)ethylene, 2-(hydroxybenzoylamido)ethylene or 2-(aminobenzoylamido)ethylene.

25. A pharmaceutical composition according to claim 14, wherein M is 1-(benzylaminocarbonyl)-ethylene, 1-(hexahydroazepinoyl)ethylene, 1-(morpholinoyl)-ethylene, 1-(heptahydro-azocinoyl)ethylene, 1-[2-(benzyloxymethylmorpholinoyl)]ethylene, 1-[2-(hydroxymethylmorpholinoyl)]ethylene, 1-(2-ethoxycarbonyl-4-methylpiperidinoyl)ethylene, 1-(2-carboxy-4-methylpiperidinoyl)ethylene or 1-(3-carboxyhexahydro-1,4-oxazepinoyl)ethylene.

26. A pharmaceutical composition according to claim 14, wherein R is naphthyl or nitro- or iodophenyl, L is NH and the asymmetric C atom in the piperidine ring has the (S)-configuration.

27. A method of inhibiting thrombin induced platelet aggregation and clotting of fibrinogen in plasma which comprises administering to a host requiring such treatment an effective amount of a compound of the formula

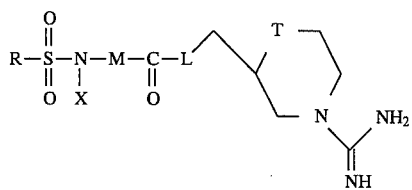

I wherein
R is aryl, heteroaryl or heterocyclyl,
L is NH or O;
X is H, —CH₂COOH, —CH₂COO—C$_{1-4}$-alkyl, —CH₂CO— (tetra- to heptamethyleneimino) or optionally N- mono- or N-di-C$_{1-4}$-alkylated —CH₂CONH₂;
M is a substituted ethylene group of the formula:
  —CH₂[R'—(CO)$_{1-2}$NH]CH—, —CH₂(benzyl-OCONH)CH— or —CH(CO—Q)CH₂—;
R' is aryl, heteroaryl, cycloalkyl or heterocyclyl,
Q is benzylamino or a tetra- to heptamethyleneimino group optionally substituted by up to 2 substituents from the group C$_{1-4}$-alkyl, COOH, —COO—C$_{1-4}$-alkyl, —CH₂OH and —CH₂O-benzyl, or a hydrate of solvate, or physiologically usable salt thereof.

28. A method according to claim 27, wherein the compound is of the formula

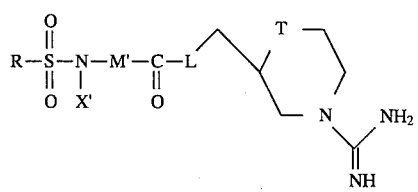

IA wherein
X' is H, —CH₂COOH, —CH₂COO—C$_{1-4}$-alkyl, —CH₂CO— tetra- to heptamethyleneimino or optionally N- mono- or N-di-C$_{1-4}$-alkylated —CH₂CONH₂, and
M' is a —CH(CO—Q')CH₂— group,
Q' is benzylamino, morpholino or tetra- to heptamethyleneimino, or a hydrate or solvate, or physiological usable salt thereof.

29. A method according to claim 27, wherein the compound is of the formula

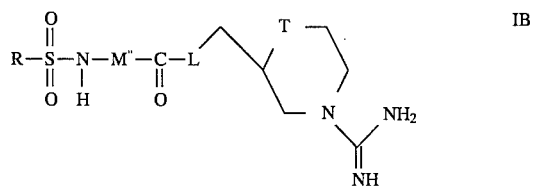

IB wherein
M" is a —CH₂[R'—(CO)$_{1-2}$NH]CH—, —CH₂(benzyl-OCONH)CH— or —CH(CO—Q")CH₂— group, and
Q" is a tetra- to heptamethyleneimino group optionally interrupted by an O or S atom and optionally substituted by up to 2 substituents selected from the group consisting of C$_{1-4}$-alkyl, COOH, —COO—C$_{1-4}$-alkyl, —CH₂OH and —C₂O-benzyl.

30. A method according to claim 27, wherein the compound is selected from the group consisting of:

(S)-N-[(RS)-1-amidino-3-piperidinyl methyl]hexadyro-β-(2-naphthylsulfonamido)-γ-oxo-1H-1-azepinebutyramide, (S)-N-[[(RS)-1-amidino-3-piperidinyl]methyl]hexahydro-β-2-naphthysulfonamido-γ-oxo-1(2H)-azocine butyramide, (2RS,4R)-1-[N⁴-[[(S)-1-amidino-3-piperidinyl]methyl]-N²-(2-naphthylsulfonyl)-L-asparaginyl]-4-methyl-2-piperidine carboxylic acid, (S)-N-[(RS)-1-amidino-3-piperidinylmethyl]-3-benzylcarbamoyl-3-(2-naphthylsulfonamido)proprionamide, (R)-N-[(RS)-1-amidino-3-piperidinyl methyl]-3-benzylcarbamoyl-3-(2-naphthylsulfonamido)propionamide, (S)-N-[[(RS)-1-amidino-3-piperidinyl]methyl]-β-2-naphthylsulfonamido-γ-oxo-4-morpholinebutyramide, (R)-N-[[(RS)-1-amidino-3-piperidinyl]methyl]hexahydro-β-2-naphthylsulfonamido-γ-oxo-1H-azepinebutyramide, (βS,2RS)-N-[[(RS)-1-amidino-3-piperidinyl]methyl]-2-benzyloxymethyl-β-2-naphthylsulfonamido-γ-oxo-4-morpholinebutyramide, (βS,2RS)-N-[[(RS)-1-amidino-3-piperidinyl]methyl]-2-hydroxymethyl-β-2-naphthylsulfonamido-γ-oxo-4 morpholine butyramide,

[(S)-1-[[[(RS)-1-amidino-3-piperidinyl]methyl]carbamoyl-2-(2-naphthylsulfonamido)-ethylcarbamate, O-[[(S)-1-[[[(RS)-1-amidino-3-piperidinyl]methyl]carbamoyl]-2-(2-naphthylsulfonamido)ethyl]carbamoyl]benzoic acid, (S)-2-N-[o-(benzyloxy)benzamido]-3-(2-naphthylsulfonamido)-N-[[RS)-1-amidino-3-piperidinyl]methyl]propionamide, (R)-N-(S)-1-[[[(RS)-1-amidino-3-piperidinyl]methyl]carbamoyl]-2-(2-naphthylsulfonamido)-2-piperidine carboxamide, (S)-N-[[(RS)-1-amidino-3-piperidinyl]methyl]-2-(2-hydroxybenzamido)-3-(2-naphthylsulfonamido)propionamide, N-[(S)-1-[[[(S)-1-amidino-3-piperidinyl]methyl]carbamoyl]-2-(2-naphthylsulfonamido)ethyl]-o-aminobenzamide, ethyl(2RS,4R)-1-[(S)-3-[[[(S)-1-amidino-3-piperidinyl]methyl]carbamoyl]-2-(2-naphthylsulfonamido)proprionyl]-4-methyl-2-piperidine carboxylate, and (R)-4-[(S)-3-[[[(S)-1-amidino-3 -piperidinyl]methyl]car-
bamoyl]-2-(2 -naphthysulfonamido)propionyl]hexahy-
dro-1,4 -oxazepine-3-carboxylic acid.

31. A method according to claim 28, wherein X' is H.

32. A method according to claim 27, wherein X is other than H.

33. A method according to claim 27, wherein R is naphthyl, hydroxynaphthyl, 4-biphenyl, 2-anthryl, iodophenyl, nitrophenyl, benzyloxyphenyl, dimethoxyphenyl, 4-methoxy- 2,3,6-trimethylphenyl, 2,4,6-triisopropylphenyl, carboxyphenyl, methoxycarbonylphenyl, benzyloxynaphthyl, phenylsulfonylphenyl, hexahydroazepinoylphenyl or t-butylphenyl.

34. A method according to claim 27, wherein R is 3 -methyl-8-quinolyl, 5-(1-methyl-5-trifluoromethylpyrazol-3-yl)-2-thienyl or benzothienyl.

35. A method according to claim 27, wherein R is 3-methyl-1,2,3,5-tetrahydro-8-quinolyl.

36. A method according to claim 27, wherein X is H or —CH$_2$COOH.

37. A method according to claim 27, wherein M is 2-(carboxybenzoyl-amido)ethylene, 2-(benzyloxybenzoylamido)ethylene, 2-(2-piperidinecarboxamido)ethylene, 2-(hydroxybenzoylamido)-ethylene or 2-(aminobenzoylamido)ethylene.

38. A method according to claim 27, wherein M is 1 -(benzylaminocarbonyl)-ethylene, 1-(hexahydroazepinoyl-)ethylene, 1-(morpholinoyl)-ethylene, 1-(heptahydroazocinoyl)ethylene, 1-[2-(benzyloxy methylmorpholinoyl)]ethylene, 1-[2-(hydroxymethylmorpholinoyl)]ethylene, 1-(2 -ethoxycarbonyl-4-methylpiperidinoyl)-ethylene, 1-(2-carboxy-4-methylpiperidinoyl)ethylene or 1-(3-carboxy-hexahydro-1,4-oxazepinoyl)ethylene.

39. A method according to claim 27, wherein R is naphthyl or nitro- or iodophenyl, L is NH and the asymmetric C atom in the piperidine ring has the (S)-configuration.

40. A compound according to claim 2, wherein X' is H or —CH$_2$COOH.

41. A pharmaceutical composition according to claim 15, wherein X' is H or —CH$_2$COOH.

42. A method according to claim 28, wherein X' is H or —CH$_2$COOH.

43. A compound of the formula

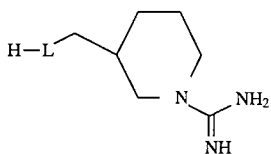

III wherein

L is NH or O.

44. A compound of the formula

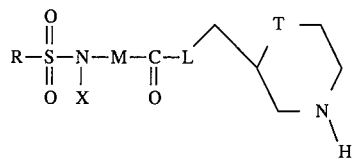

IV wherein

R is aryl, heteroraryl or heterocyclyl;

L is NH or O;

X is H, —CH$_2$COOH, —CH$_2$COO—C$_{1-4}$-alkyl, —CH$_2$CO— (tetra- to heptamethyleneimino) or optionally N- mono- or N-di-C$_{1-4}$-alkylated —CH$_2$CONH$_2$;

M is a —CH$_2$[R'(CO)$_{1-2}$NH]CH—, —CH$_2$(benzyl-OCONH)CH— or —CH(CO—Q)CH$_2$— group;

R' is aryl, heteroaryl, cycloalkyl or heterocyclyl; and

Q is benzylamino or a tetra- to heptamethyleneimino group optionally substituted by up to 2 substituents from the group C$_{1-4}$-alkyl, COOH, —COO—C$_{1-4}$ alkyl, —CH$_2$OH and —CH$_2$O-benzyl.

45. A compound of the formula

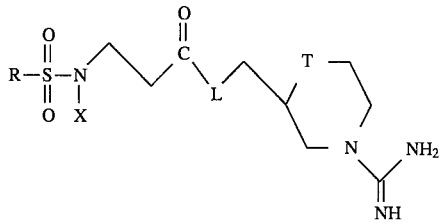

V wherein

R is aryl, heteroaryl or heterocyclyl;

L is NH or O; and

X is H, —CH$_2$COOH, —CH$_2$COO—C$_{1-4}$-alkyl, —CH$_2$CO— (tetra- to heptamethyleneimino) or optionally N- mono- or N-di-C$_{1-4}$-alkylated —CH$_2$CONH$_2$.

* * * * *

UNITED STATES PATENT AND TRADEMARK OFFICE
CERTIFICATE OF CORRECTION

PATENT NO. : 5,532,232
DATED : July 2, 1996
INVENTOR(S) : Ackermann et al.

Page 1 of 3

It is certified that error appears in the above-indentified patent and that said Letters Patent is hereby corrected as shown below:

In Claim 2, Column 37; Claim 15, Column 39; and Claim 28, Column 41, replace formula IA with:

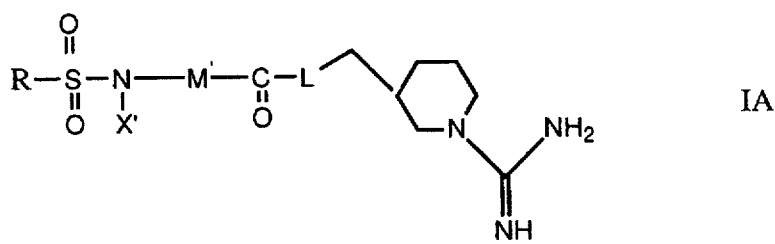

IA

In Claim 4, Column 37; Claim 17, Column 39; and Claim 29, Column 42, replace formula IB with:

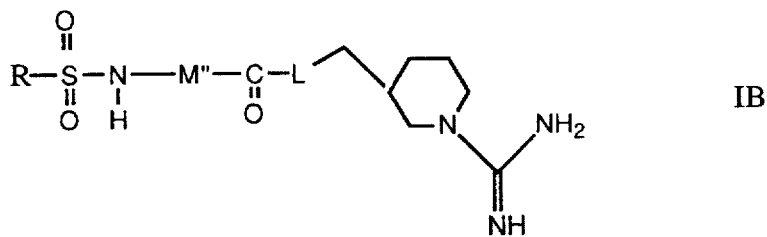

IB

UNITED STATES PATENT AND TRADEMARK OFFICE
CERTIFICATE OF CORRECTION

PATENT NO. : 5,532,232
DATED : July 2, 1996
INVENTOR(S) : Ackermann et al.

Page 2 of 3

It is certified that error appears in the above-indentified patent and that said Letters Patent is hereby corrected as shown below:

In Claim 44, Column 44, replace formula IV with:

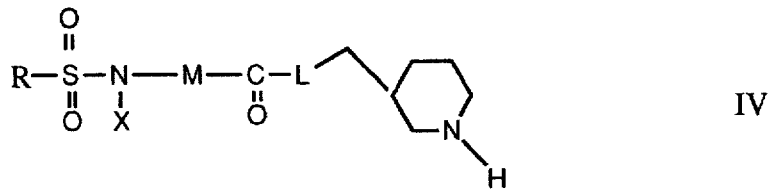

IV

In Claim 45, Column 44, replace formula V with:

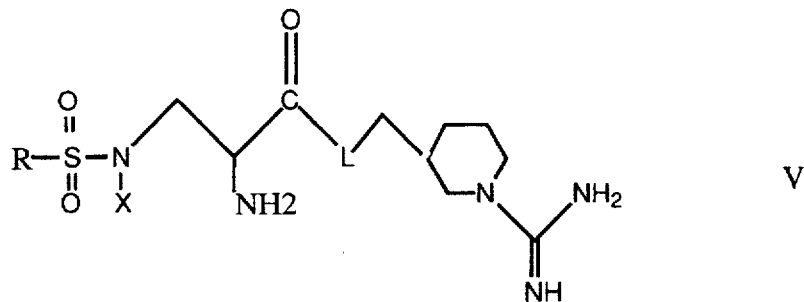

V

UNITED STATES PATENT AND TRADEMARK OFFICE
CERTIFICATE OF CORRECTION

PATENT NO. : 5,532,232
DATED : July 2, 1996
INVENTOR(S) : Ackermann et al.

It is certified that error appears in the above-indentified patent and that said Letters Patent is hereby corrected as shown below:

In Claim 1, Column 37, Line 7, change "OR" to -- or --.

In Claim 1, Column 36; Claim 14, Column 39; and Claim 27, Column 41, replace formula I with:

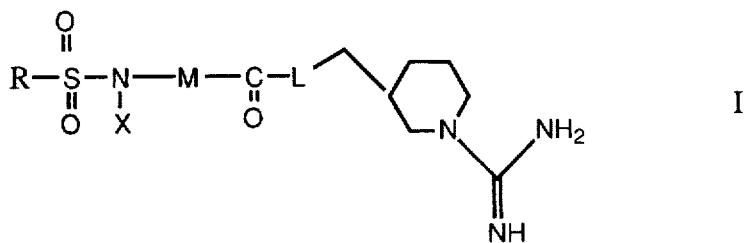

Signed and Sealed this

Thirtieth Day of September, 1997

Attest:

BRUCE LEHMAN

Attesting Officer

Commissioner of Patents and Trademarks